US007166695B2

(12) United States Patent
Krantz et al.

(10) Patent No.: US 7,166,695 B2
(45) Date of Patent: Jan. 23, 2007

(54) AFFINITY MARKERS FOR HUMAN SERUM ALBUMIN

(75) Inventors: Alexander Krantz, San Francisco, CA (US); Wolin Huang, Foster City, CA (US); Arthur M. Hanel, San Francisco, CA (US); Darren L. Holmes, Montreal (CA); Dominique P. Bridon, Ville Mont-Royal (CA)

(73) Assignee: ConjuChem Biotechnologies Inc., Montreal (CA)

( * ) Notice: Subject to any disclaimer, the term of this patent is extended or adjusted under 35 U.S.C. 154(b) by 0 days.

(21) Appl. No.: 10/934,841

(22) Filed: Sep. 2, 2004

(65) Prior Publication Data

US 2005/0037974 A1    Feb. 17, 2005

Related U.S. Application Data

(62) Division of application No. 09/530,298, filed as application No. PCT/US98/23705 on Nov. 6, 1998, now abandoned.

(60) Provisional application No. 60/077,927, filed on Mar. 13, 1998, provisional application No. 60/064,705, filed on Nov. 7, 1997.

(51) Int. Cl.
*C07K 7/06* (2006.01)
(52) U.S. Cl. ................. 530/330; 530/327; 530/328; 530/329; 530/345; 435/4; 435/7.5
(58) Field of Classification Search ............ 514/15–19; 530/327, 328, 329, 330, 345; 435/4
See application file for complete search history.

(56) References Cited

U.S. PATENT DOCUMENTS

| | | | |
|---|---|---|---|
| 3,862,928 A | 1/1975 | De Wied et al. | |
| 4,808,705 A | 2/1989 | Ferris | |
| 4,933,288 A | 6/1990 | Greenfield | |
| 4,981,979 A | 1/1991 | Sivam | |
| 5,116,944 A | 5/1992 | Sivam et al. | |
| 5,130,116 A | 7/1992 | Woo et al. | |
| 5,250,662 A | 10/1993 | Chang | |
| 5,302,697 A | 4/1994 | Goodey et al. | |
| 5,571,681 A | 11/1996 | Janda | |
| 5,612,034 A | 3/1997 | Pouletty et al. | |
| 5,741,893 A | 4/1998 | Hsia | |
| 5,897,863 A | 4/1999 | Robson et al. | |
| 5,945,033 A | 8/1999 | Yen | |
| 6,203,820 B1 | 3/2001 | Vickery | |

FOREIGN PATENT DOCUMENTS

| WO | WO 95/10302 | 4/1995 |
|---|---|---|
| WO | WO 97/22617 | 6/1997 |
| WO | WO 97/25074 | 7/1997 |
| WO | WO 97/29372 | 8/1997 |
| WO | WO 98/11437 | 3/1998 |

OTHER PUBLICATIONS

Szekerke, M. FEBS Letters 44, 160-163, 1974.*
Inagawa, Chemical Abstracts 121, 77796p, 1994.*
Sjobbring, U. (Sep. 1992) "Isolation and Molecular Characterization of a Novel Albumin-Binding Protein from Group G Streptococci" Infect. Immun. 60 (9): 3601-3608.
Ghinea et al. (Mar. 25, 1989) "Endothelial Albumin Binding Proteins are Membrane-Associated Components Exposed on the Cell Surface" J. of Biol. Chem. 264 (9): 4755-4758.
Ahlfors, et al. (1995) "Plasma Fluorescein Binding and Transcapillary Fluorescein Escape Rate in Renal Failure Associated with Diabetes" American Journal of Kidney Diseases 25 (4): 543-547.
Nagataki et al. (1985) "Binding of Fluorescein Monoglucuronide to Human Serim Albumin" Investigative Opthalmology and Visual Science 26 (8): 1175-1178.
Rowland, et al. (1980) "Clinical Pharmacokinetics: Concepts and Applications" Lea & Febiger, Philadelphia, US: 246:265.
Schnitzer et al. (Dec. 1, 1992) "Antibodies to Sparc Inhibit Albumin Binding to Sparc, GP60, and Microvascular Endothelium" American Journal of Physiology: Heart and Circulatory Physiology 32 (6): H1872-1879.
Richter et al. (1977) "Fluoro Immuno Cyto Adherence: A New Method for the Identification and Enumeration of Antigen Binding Cells" Zeitschrift Fuer Immunitaetsforschung: 351-362.
Sjolander et al. (Feb. 14, 1977) "The Serum Albumin-Binding Region of Streptococcal Protein G: A Bacterial Fusion Partner with Carrier-Related Properties" Journal of Immunological Methods 201 (1): 115-123.
Bioorganic & Medicinal Chem. Lett., 1997, 7 (11): 1371-1376.
Methods in Molecular and Cellular Biology, 1995, 6 (1): 15-25.

* cited by examiner

*Primary Examiner*—David Lukton
(74) *Attorney, Agent, or Firm*—Jones Day

(57) ABSTRACT

Methods and compositions are provided for identifying compounds having affinity or complementarity to a target molecule. Compounds according to the invention may be described by the formula $E-C_a-R-C_b-A$, wherein E is a therapeutic or diagnostic agent, R is a reactive group, $C_a$ and $C_b$ are connector groups between E and R and between R and A, respectively, and A is an affinity group comprising the sequence F-1-Y-E-E. Compounds according to the invention may be used for labeling the target molecule, particularly where the target molecule is naturally found in a complex mixture, such as a physiological fluid, like blood. By affinity labeling in vivo, the lifetime of physiologically active entities can be greatly enhanced by becoming bound to long-lived blood components. The covalently bound entity may also serve as an antagonist or agonist of a particular binding protein or as an enzyme inhibitor.

33 Claims, 20 Drawing Sheets

REACTION OF HSA WITH BIOTIN-S-(PHENYL)$p$ CONH-W-E-O-X-NH2;
QUENCH TIME = 5 SEC.

COMPETITION OF BIOTIN-OPh-CO-FIYEE-NH$_2$ (44µM)
vs. HO-Ph-CO-FIYEE-NH$_2$

"COMPETITION" TEST BETWEEN BIOTIN-OPh-F$I$YEE-NH$_2$
(44μM) AND HO-Ph-CO-F$I$YEE-NH$_2$

KINETIC STUDY BY ELISA CAPTURE

RATE OF REACTION OF 600 μM HSA WITH 100 μM BIOTIN-OPh-CONH$_2$ IN pH 7.4 PBS AT RT

RATE OF REACTION OF 100 μM BIOTIN-OPh-CO-FIYEE-NH$_2$
IN COMMERCIAL HUMAN PLASMA

RATE OF HYDROLYSIS OF 100 μM BIOTIN-OPh-CO-FIYEE-NH$_2$
IN pH 7.4 PBS AT RT

RATE OF REACTION OF 100 μM BIOTIN-OPh-CO-FIYEE-NH$_2$
WITH 600 μM HSA AT RT

AFFINITY MARKERS FOR HUMAN SERUM ALBUMIN

RELATED APPLICATIONS

This application is a DIVISIONAL application of U.S. patent application Ser. No. 09/530,298 filed Apr. 27, 2000, now abandoned which is a Section §371 National Phase of PCT/US598/23705 filed Nov. 6, 1998, which claims benefit of U.S. Provisional Patent Application Ser. No. 60/064,705 filed Nov. 7, 1997, and also claims benefit of U.S. Provisional Patent Appplication Ser. No. 60/077,927 filed Mar. 13, 1998, all of which are incorporated herein by referenced in their entirety.

FIELD OF THE INVENTION

This invention relates to libraries of affinity markers, and especially FIYEE, (SEQ ID NO:1) for human serum albumin. This invention is further related to methods of screening the affinity marker libraries, identification of specific markers and the use of the markers as delivery agents for therapeutic in vitro and in vivo diagnostic agents.

BACKGROUND OF THE INVENTION

The advent of combinatorial chemistry has provided a platform for a wide variety of opportunities. The ability to produce large libraries of different compounds means that one can screen a large array of conformations, and charge distributions for their ability to bind to other compounds to act as agonists or antagonists, in binding to specific sites of a target protein, to investigate the conformation of a particular protein site, such as an enzymatic cleft or membrane channel protein, and the like.

The existence of combinatorial chemistry affords new opportunities towards new therapies for diseases for which prior drugs are inadequate or for which there are no present successful therapies. The presently available drugs are inadequate for a wide variety of reasons, in many cases, the pharmacokinetics of the drugs. Parenteral delivery in a bolus has many constraints on its efficacy. Since most drugs have serious side effects, one is constrained as to the upper dosage level. On the other hand, drugs may undergo enzymatic modification, oxidation, degradation in the liver, secretion, and the like, so that the lifetime of the drug will be limited by the various mechanisms which serve to diminish the effective level of the drug.

Drugs which have been approved for use with humans have already been shown to be generally safe at the prescribed dosage and effective. Therefore, there are substantial advantages in being able to modify these drugs, where their safety and efficacy are not unduly altered. In this way, the economies of dealing with known entities can be achieved, while at the same time increasing the available therapeutic opportunities.

BRIEF SUMMARY OF THE INVENTION

The present invention addresses these and other problems of the prior art by providing compounds having the formula $E-C_a-R-C_b-A$. In this formula, E contains an active diagnostic moiety or pharmacophore and suitable connectors, R is a potentially reactive functional group contained within the entity and is capable of transferring an active diagnostic moiety or pharmacophore. $C_a$ and $C_b$ are connector groups between E and R and between R and A, respectively. A is any molecule or part of a molecule that possess specific binding determinants for a target molecule, such as proteins including human serum albumin. (These components of compounds according to the present invention are defined more fully below.) In some compounds according to the invention, affinity group A comprises a sequence of amino acid residues $-O_1-O_2-X_1-X_2-B$ in which the amino acid residues are independently selected from the group of all twenty naturally occurring amino acids. A particularly preferred sequence is FIYEE. (SEQ ID NO:1) Preferred compounds according to the invention include biotin-S-Ph-C(O)-FIYEE-NH$_2$, biotin-OPh-C(O)-FIYEE-NH$_2$, LC-biotin-S-Ph-C(O)-FIYEE-NH$_2$, biotin-Gly-OPh-C(O)-FIYEE-NH$_2$, fluorescein-Gly-OPh-FIYEE-NH$_2$, LC-biotin-OPh-C(O)-FIYEE-NH$_2$, argatroban-AEA$_3$-βAla-Gly-OPh-C(O)-FIYEE-NH$_2$ and fluorescein-thiourea-AEA$_3$-Gly-OPh-C(O)-FIYEE-NH$_2$, where LC is (for "long chain") has the formula $-NH-(CH_2)_n-C(O)-$, where n is an integer between 1 and 25. These compounds can bind to specific proteins in vivo and enhance the half lives of diagnostic and therapeutic agents as well as control side effects.

The present invention is also directed to methods for screening for the affinity of a compound for active sites on a target molecule. In methods according to the invention, the target molecule is immobilized on a test substrate and then incubated with the compound under conditions that support interaction (i.e., noncovalent binding) between the compound and the active sites on the target molecule. Then, the interaction between the active sites and the compound is quenched. Thereafter, an assay can be performed to detect the activity of the target molecule.

This invention could be seen as a replacement for some antibody uses, particularly in the field of in vitro diagnostic or in vivo therapy. The present invention is an improvement on U.S. Pat. No. 5,612,034 (Pouletty, et al.) teaching the art of labeling protein in vivo in a nonspecific manner since the present invention extends the life of the drug and controls its distribution, thereby limiting its side effects.

BRIEF DESCRIPTION OF THE DRAWINGS

This invention will be better understood by reference to the figures, in which.

DETAILED DESCRIPTION OF THE INVENTION

Figure 1:
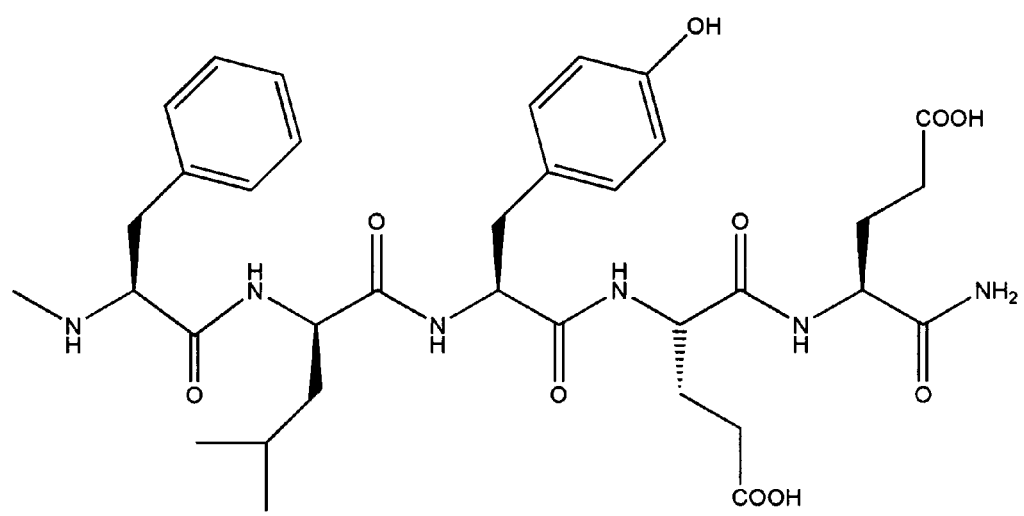
FIG. 1 shows the structural formula of the most preferred affinity group of the invention, FIYEE (SEQ ID NO:1).

In order to ensure a complete understanding of the invention, we first provide definitions of terms used in this patent. We then discuss the results of specific screening experiments used to determine affinity groups for labeling human serum albumin (HSA). We discuss the specific affinity groups identified by the screening and the specific entity, reactive groups, and connecting groups used in the library screening experiments. We then discuss more general target molecules, affinity groups, reactive groups, connecting groups and entities that fall within the scope of the invention. Finally, we present experimental results for the synthesis of the libraries used in the present-invention together with the experimental screening results and the results of experiments characterizing the entity/target-molecule binding.

DEFINITIONS

Entity: a segment of an affinity labeling reagent that is to be covalently attached to the target molecule. Generally, the entity includes an active diagnostic moiety or pharmacophore and suitable connectors. Examples of possible diagnostic or therapeutic agents are provided below.

Affinity Group: any molecule or part of a molecule that posses specific binding determinants for a target molecule. In the context of this filing, the affinity group includes oligomeric moieties such as peptides, carbohydrates and nucleotides and combinations thereof that confer affinity to the target molecule by virtue of their complementarity for specific sites of the target. Such oligomeric units distinguish affinity groups from connectors and reactive groups, all of which are components of the entity in rate. Since the activities of affinity reagents are measured in terms of the rate by which they covalently label their targets, any increase in rate above 100% (factor of 2) conferred by such oligomeric units, relative to a standard molecule lacking such oligomeric units, relative to a standard molecule lacking an oligomeric group complementary to the target, defines these groups as affinity groups in this application. According to the invention, suitable affinity groups for labeling human serum albumin include oligomeric molecules including peptides, carbohydrates and nucleotides and combinations thereof.

Reactive Group: generally a potentially reactive organic functional group contained within the entity capable of transferring an active diagnostic moiety or pharmacophore. Reactive groups according to the invention may be bonded to the affinity group by a first connecting group. The reactive group may be bonded to the entity by a second connecting group and in this case, the bond between the reactive group and the second connecting group must be able to cleave allowing the second connecting group to bond to the target molecule.

Reactive Functional Group: generally any group that may be incorporated in the molecules of the invention either between the reactive group and the affinity group or between the reactive group and the entity.

Target Molecules: any molecules to which affinity groups are complementary by virtue of specific binding determinants and to which the whole entity may react to form a covalent bond. Human serum albumin is the most preferred target molecule; examples of other preferred target molecules are discussed below.

In Vitro Diagnostic Agent: any molecule that finds use in in vitro diagnostic analysis.

In Vivo Diagnostic Agent: any molecule that finds use in in vivo diagnostic analysis.

Diagnostic Agents: Diagnostic agents include agents used in diagnostic techniques such as positron emission tomography (PET), computerized tomography (CT), single photon emission computerized tomography (SPECT), magnetic resonance imaging (MRI), nuclear magnetic imaging (NMI), fluoroscopy and ultrasound, fluorphors, chromophors and chemiluminophors.

Diagnostic agents of interest include contrast agents, radioisotopes of such elements as iodine (I), including $^{123}$I, $^{125}$I, $^{131}$I, etc., barium (Ba), gadolinium (Gd), technetium (Tc), including $^{99}$Tc, phosphorus (P), including $^{31}$P, iron (Fe), manganese (Mn), thallium (Tl), chromium (Cr), including $^{51}$Cr, carbon (C), including $^{11}$C, or the like, fluorescently labeled compounds, and fluorine containing chemicals useful in ultrasound, etc.

Therapeutic Agent: any molecule that has a therapeutic (i.e., healing or curative) effect. Therapeutic agents are agents that have a therapeutic effect. Therapeutic agents include drugs, antibiotics, antiinfectives, anti-cancer agents, pain management agents, cardiovascular drugs (antithrombotics, anticoagulants, anti-platelet, protease inhibitors, calcium channel blockers, etc.), anti-inflammatory agents, anti-proliferative drugs, oligonucleotides (sense and antisense). Therapeutic agents are generally drugs or small molecules having a molecular weight less than 2000.

Specific Affinity Groups for Human Serum Albumin

Using library screening techniques according to the invention and exemplified below, the inventors have identified a series of compounds that are useful for attaching an entity (usually a diagnostic or therapeutic agent) to human serum albumin (HSA). In one embodiment of the present invention, the compounds have the formula, E-$C_a$—R—$C_b$-A, where E is the entity to be attached to the target molecule, $C_a$ and $C_b$ are connecting groups, R is a reactive group and A is an affinity group. $C_b$ and $C_a$ are also referred to herein as the first connecting group and the second connecting group, respectively. As discussed below, the connecting groups $C_a$ and $C_b$ may not be required and the invention also covers compounds of the formula E-R—$C_b$-A, E-$C_a$—R-A and E-R-A.

As exemplified below, the inventors synthesized an affinity labeling library of general formula E-R—$O_1$—$O_2$—$X_1$—$X_2$—B—$NH_2$ and screened this library of compounds against HSA as the target molecule. For the diagnostic screening, E was a biotin group; R was selected from —S-Ph-C(O)— (example 1 below), —O-Ph-C(O)— (example 2) and —N-Ph-C(O)— (example 3); and $O_1$, $O_2$, $X_1$, $X_2$ and B are amino acid residues selected from glutamic acid, glutamine, arginine, methionine, serine, tyrosine, leucine, phenylalanine and tryptophan. The inventors also synthesized an embodiment of the invention of the formula E-$C_a$—R—$O_1$—$O_2$—$X_1$—$X_2$—B—$NH_2$ where E is biotin and $C_a$ is —NH—$(CH_2)_5$—C(O)—.

The library screening results indicated that library members exhibiting enhanced binding to HSA included the following amino acid residues:
  $O_1$ is selected from phenylalanine, arginine, glutamine, tyrosine, glutamic acid and tryptophan;
  $O_2$ is selected from leucine, arginine, glutaric acid, tryptophan and phenylalanine;
  $X_1$ is selected from phenylalanine, tryptophan, methionine and tyrosine;
  $X_2$ is selected from serine, arginine and glutamic acid; and
  B is selected from serine, arginine and glutamic acid.

Analysis of these results suggest that hydrophobic residues are preferred at both the $O_1$ and $O_2$ positions, with large hydrophobic residues being more preferred; hydrophobic residues are also preferred at the $X_1$ position. Although the results do not appear to demonstrate any clear preference for different residues at the $X_2$ and B positions, based on other considerations discussed below, it appears that more polar, charged amino acids are preferable.

To reduce the possibility of degradation of a peptide affinity group (i.e., where two or more of the residues in $O_1$—$O_2$—$X_1$—$X_2$—B are amino acids), one or more D-amino acid residues can be included in an L-amino acid peptide or one or more L-amino acid residues can be included in an D-amino acid peptide. For example, including a D-amino acid residue at position $O_2$, $X_1$, or $X_2$ in an L-amino acid peptide (or vice versa) will yield two D-L bonds, which may reduce degradation. In a preferred embodiment of this invention, the inventors included a D-amino acid residue at the $O_2$ position and included L-amino acid residues at the other positions.

Preferred combinations of the $O_1$ and $O_2$ residues are as follows:
  $O_1$ is phenylalanine and $O_2$ is D-leucine;
  $O_1$ is arginine and $O_2$ is D-arginine;
  $O_1$ is glutamine and $O_2$ is D-glutamic acid;
  $O_1$ is glutamic acid and $O_2$ is D-tryptophan;
  $O_1$ is tryptophan and $O_2$ is D-tryptophan; and
  $O_1$ is tryptophan and $O_2$ is D-glutamic acid.

Figure 4:
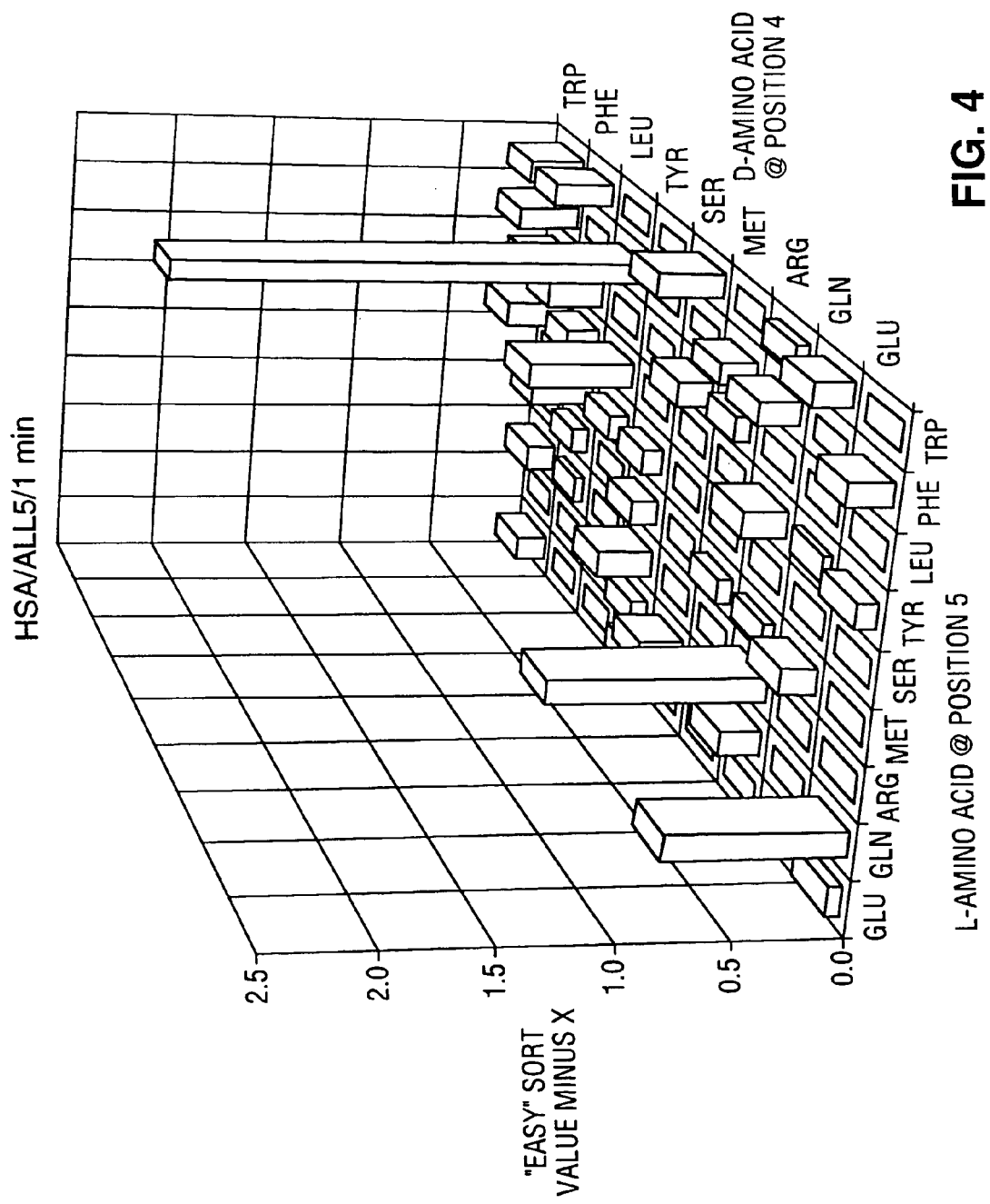
FIG. 4 shows optical density measurement for the screening of a library according to the present invention at the level of 81 compounds per well with a 1 minute quenching time

In the most preferred combination, $O_1$ is phenylalanine and $O_2$ is leucine as determined by the analysis of FIG. 4. FIG. 4 represents the rate of addition, expressed as optical density units, of library members on HSA. An elevated value for the optical density is representative of a larger amount of biotin on HSA at a given time. A larger amount of biotin on HSA at a given time is representative of a higher specificity of a library member or members for a given site, resulting in an accelerated addition of biotin on the target site.

The preferred amino acids at the $X_1$, $X_2$, and B positions are tyrosine, glutamic acid and glutamic acid respectively. The most preferred affinity group is FlYEE (SEQ ID NO:1), where F is phenylalanine, l is D-leucine, Y is tyrosine, and E is glutamic acid.

In a preferred embodiment, the B position amino acid residue is the C-terminal amino acid. In another preferred embodiment, the B position amino acid residue exists in its carboxamide form rather than in the carboxylic acid form. In this preferred embodiment the -FlYEE affinity group (SEQ ID NO:1) has the structural formula shown in FIG. 1.

The screening experiments described herein identified the affinity groups discussed above and these screening results indicate that the affinity groups may preferentially bind to HSA and may therefore be useful in directing specific entities to covalently bind to HSA. Specific experiments demonstrating such specific binding are described in the EXPERIMENTS section.

Reactive Groups (R)

A preferred affinity marker compound of the present invention includes a reactive group (R) in addition to the affinity group described above. The reactive group may be connected through to the affinity group via a first connecting group ($C_b$) or, preferably, is bonded directly to the affinity group.

Generally the reactive group, R, will include a reactive functional group selected from carboxy, phosphoryl, alkyl esters, thioesters, phosphoesters, ortho esters, imidates, mixed anhydrides, disulphides, amides and thioamines. It is preferred that the reactive group is stable in an aqueous environment. In a preferred embodiment, the reactive group will include an aromatic moiety, preferably a substituted or unsubstituted phenyl group.

Generally, the bond between the reactive group and the affinity group should be a thermodynamically stable, but potentially reactive covalent bond (i.e., irreversible bond). In a preferred embodiment of the invention, the reactive group is bonded directly to the $O_1$ amino acid of the affinity group.

In a more preferred embodiment, the reactive group is bonded to the $O_1$ amino acid of the affinity group by an amide linkage.

In one embodiment of the invention, the reactive group has the formula —X—$R_1$—C(O)—, where X is sulfur, oxygen, or nitrogen; $R_1$ includes a substituted or unsubstituted aromatic group; and C(O) represents a carboxyl group. Also suitable is a reactive group of the formula —X—$R_1$—C(S)—, where X is sulfur, oxygen, or nitrogen; $R_1$ includes a substituted or unsubstituted aromatic group; and C(S) is a thiocarbonyl group. Preferably, X is sulfur or oxygen. In another preferred embodiment, X is directly bonded to an aromatic carbon in the $R_1$ group. In a more preferred embodiment, $R_1$ is a substituted or, preferably, an unsubstituted phenyl. In this context, by "substituted phenyl", we mean a phenyl group bearing substituents such as halogen, NO2, SO2NH2, SO2NHF, CF3, CCl3, CBr3, C=N, SO3H, CO2H, CHO, NHR, OH, NHCOCH3, OCH3, CH3, and CH2CH3, in addition to the —X— and —C(O)— groups explicitly laid out in the formula. In a more preferred embodiment, $R_1$ is unsubstituted phenyl and the —X— and —C(O)— substituents are bonded to the phenyl group in a para configuration. In another preferred embodiment of the invention, the reactive group carboxyl group is directly bonded to the $O_1$ amino acid of the affinity group, generating a stable amide bond.

In another embodiment of the invention, the reactive group is attached to the affinity group via a first connecting group. In this embodiment, suitable connecting groups may be as described below in the "General Connecting Groups" section.

Entity (E)

The reactive group may either be bonded directly to the entity or connected thereto via a second connecting group ($C_a$). The entity may generally be any fragment or moiety that is desired to be covalently bonded to the target molecule and preferred entities include a variety of pharmacophore and active diagnostic agents that are described in detail in the "General Entities" section below. In a preferred embodiment, the entity includes a biotin group.

When compounds according to the invention covalently react with to the target molecule, the covalent bond between the entity and the reactive group cleaves, liberating an -RL-A or RL-$C_b$-A fragment, wherein RL is R after reaction with a nucleophile, whereby an entity/target-molecule covalent bond forms to attach the entity to the target molecule. This mechanistic understanding of the chemistry is useful in determining which entity/reactive-group bonds are most suitable. In a preferred embodiment of the invention, the entity is bonded to the reactive group by an amide, or more preferably, an ester or thioester bond.

In a preferred embodiment of the invention, the entity forms a covalent bond to an amino group on the target molecule and in this case an ester or thioester bond between the entity and the reactive group is preferred. However, in other embodiments of the invention, the entity can form covalent bonds to hydroxyl, thiol, or other available functional groups on the target molecule.

If the entity is to form a covalent bond with a hydroxyl group on the target molecule, it is preferred that the entity bonds to the reactive group by an ester bond. If the entity is to form a covalent bond with a thiol group on the target molecule, it is preferred that the entity is bonded to the reactive group by a thioester or disulfide bond.

Second Connecting Group ($C_a$)

Typical connecting groups that may be used are described in detail in the "General Connecting Groups" section below. In a preferred embodiment, the second connecting group LC (for "long chain") has the formula —NH—$(CH_2)_n$—C(O)—, where n is an integer between 1 and 25. In a more preferred embodiment, the second connecting group has the formula —NH—$(CH_2)_5$—C(O)— and —NH—$CH_2$—C(O)—. When a second connecting group is present, the mechanism for bonding the entity to the target molecule includes the breaking of the bond between the second connecting group and the reactive group and the formation of a bond between the second connecting group and a functional group on the target molecule. In this case, the entity will be attached to the target molecule via the second connecting group. One effect of the presence of the second connecting group is that the entity may be held sterically clear of the target molecule after it has been covalently attached; that is, the entity ends up tethered to the target molecule via the second connecting group. This aspect of the invention may be important in maintaining the activity of a therapeutic agent that may lose activity if it is too closely attached to the target molecule.

Preferred Embodiments

The following compounds are preferred embodiments of the present invention: A compound selected from the group consisting of biotin-S-Ph-C(O)-FIYEE-$NH_2$, biotin-OPh-C(O)-FIYEE-$NH_2$, LC-biotin-S-Ph-C(O)-FIYEE-$NH_2$, biotin-Gly-OPh-C(O)-FIYEE-$NH_2$, fluorescein-Gly-OPh-FIYEE-$NH_2$, LC-biotin-OPh-C(O)-FIYEE-$NH_2$, argatroban-$AEA_3$-βAla-Gly-OPh-C(O)-FIYEE-$NH_2$, and fluorescein-thiourea-$AEA_3$-Gly-OPh-C(O)-FIYEE-$NH_2$.

Use of Preferred Embodiments to Attach the Entity to HSA

Figure 2:
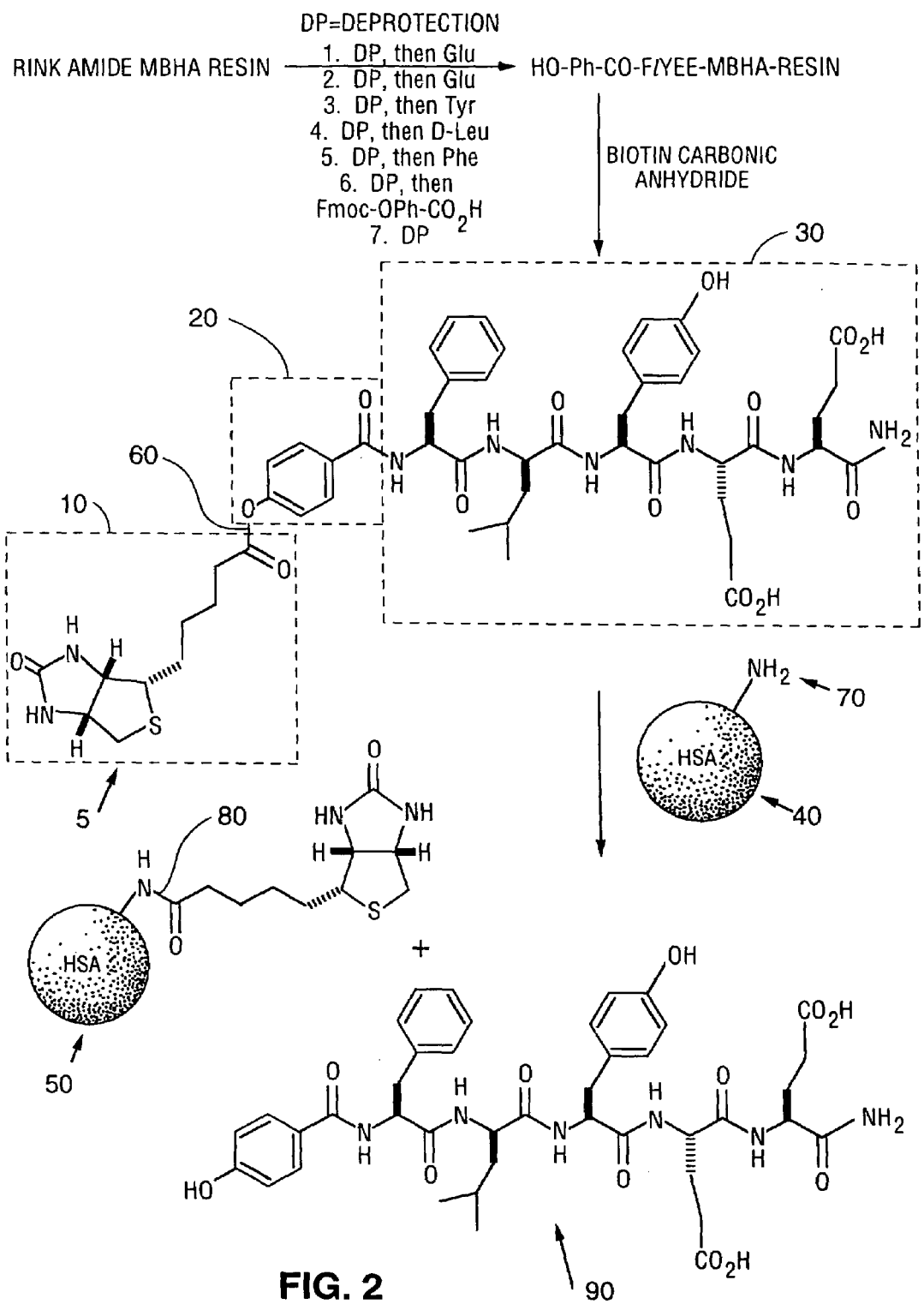
FIG. 2 shows a reaction scheme for the use of a preferred embodiment of the invention for covalently attaching biotin to HSA.

FIG. 2 shows the reaction scheme for the use of a preferred embodiment of the present invention 5 to attach a biotin group 10 (the entity) to HSA 40 (the target molecule). In the preferred embodiment shown in FIG. 2, the reactive group 20 is an —O-Ph-C(O)— group and the affinity group 30 is FIYEE (SEQ ID NO:1). The entire molecule composed of 5, 10, 60, 20 and 30 is referred to here as an affinity labeling reagent or drug affinity label conjugate. To form the target-molecule/entity complex 50, the entity/reactive functional group bond 60 cleaves and an amine group 70 on the target molecule 40 forms an amide bond 80 via a $B_{AC}2$ mechanism with the entity 10. The reactive-group/affinity-group molecule 90 is liberated. The specific experimental conditions and product characterization results for this reaction are described in detail in the "Examples" section.

General Target Molecules

Blood proteins are an important class of target molecules. Target proteins may be long lived in that they have a half life of at least about 12 hours, preferably at least about 48 hours, more preferably at least about 5 days. Preferred target proteins, either individually or as part of cells, include the surface membrane proteins of erythrocytes, particularly glycophorin A and B and 3, and C, T or B cell surface proteins, such as CD3, B7, p28, CTLA-4, CD34, Thy1, CD4, CD8, LFA1, CD5, sIgE, sIgM, platelet proteins, such as IIb/IIIA, leukocyte surface membrane proteins, serum albumin, immunoglobulins, particularly IgG and IgM, apolipoproteins, such as LDL, HDL and VLDL, and proteins associated with chylomicrons, endothelial cell surface proteins, such as integrins, adhesion proteins, etc. Cells for targeting according to the invention include platelets, erythrocytes, endothelial cells, T cells or subsets thereof, B cells or subsets thereof, other leukocytes, such as macrophages, monocytes, neutrophils, basophils, NK cells, eosinophils, stem cells, such as hematopoietic stem cells, tumorous or malignant cells, infected cells, such as virally infected, e.g., retroviruses such as HIV, DNA viruses, such as hepatitis B or C virus, etc. The cells may be fixed or mobile.

A number of proteins of interest have numerous reactive functionalities for reaction ex vivo or in vivo. For example, human serum albumin, glycophorins, thrombin, adenylate kinase, plasminogen, β-lactamase, ACE, glutathione transferase, HMG CoA reductase, gastric lipase, and lecithin: cholesterol acyl transferase have active amino groups for conjugation. Cathepsin cysteine proteases and cytosolic phospholipase $A_2$ have numerous thiol groups for conjugation.

General Affinity Groups

For the most part, the affinity group A will be oligomeric and, therefore, various types of affinity groups which find use in the invention include, for example, oligopeptides, oligonucleotides, oligosaccharides, combinations thereof, or the like. Affinity groups exhibit an affinity through non-covalent binding and association with biologically active molecules. Generally, the affinity groups represented in any particular library will be of a common type. Oligomeric affinity groups will be characterized by their ready synthesis as a combinatorial library, so that the synthetic chemistry is substantially repetitive with the addition of each monomer unit to the growing oligomer. Also, methods will be available for analyzing the composition and/or sequence of the oligomeric affinity group.

Alternatively, the affinity group may comprise small synthetic organic molecules having a molecular weight of at least about 200, and not more than about 5,000, generally ranging from about 250 to 2,000.

Generally, the oligomers employed will have at least 3 monomeric units and usually fewer than 20 monomeric units. The oligomers usually have at least 4, but fewer than 12 monomeric units and more preferably fewer than 10 monomeric units. Most preferably, the oligomers have between 4 to 8 monomeric units. The monomer units comprising an oligomeric affinity group may be naturally occurring or synthetic, generally being from about 2 to 30 carbon atoms, usually from about 2 to 18 carbon atoms and preferably from about 2 to 12 carbon atoms.

For affinity groups in the library, one or more monomeric units of the oligomer may remain constant, to reduce the overall complexity of the combinatorial library.

If the affinity group is an oligopeptide, the amino acid monomers may be naturally occurring or synthetic. Conveniently, the naturally occurring L-α-amino acids will be used, although the D-enantiomers may also be employed.

While the amino acid monomers of the oligomer may be any one of the 20 naturally occurring amino acids in either the L- or D-configuration, the amino acids employed will preferentially be free of reactive functionalities, particularly reactive functionalities which would react with the reactive functionality (R) of the affinity label compound. Therefore, the amino acids used in the invention will usually be free of reactive amino groups, frequently also being free of thiol groups. Of particular interest are such amino acids as alanine (A), glycine (G), proline (P), valine (V), serine (S), phenylalanine (F), isoleucine (I) and leucine (L) or uncharged polar amino acids like methionine (M). Other suitable amino acids include glutamate, aspartate and aromatic amino acids, such as histidine (H), tryptophan (W), tyrosine (Y), and arginine (R).

Amino acid monomers of the oligomeric affinity group may also be synthetic. Thus, any unnatural or substituted amino acids of from 4 to 30, usually from 4 to 20, carbon atoms may be employed. Of particular interest are the synthetic amino acids β-alanine and γ-aminobutyrate or functional group protected amino acids such as O-methyl-substituted threonine (T), serine (S), tyrosine (Y), or the like. Various synthetic peptides are disclosed in Stewart, et al., *Solid Phase Peptide Synthesis*, W.H. Freeman, Co., San Francisco (1969); Bodanszky, et al., *Peptide Synthesis*, John Wiley and Sons, Second Edition (1976); J. Meienhofer, *Hormonal Proteins and Peptides,* 2: 46, Academic Press (1983); Merrifield, *Adv. Enzymol.* 32: 221–96 (1969); Fields, et al., *Int. Peptide Protein Res.,* 35: 161–214 (1990) and U.S. Pat. No. 4,244,946 for solid phase peptide synthesis and Schroder, et al., *The Peptides*, Vol. 1, Academic Press (N.Y.) (1965), each of which is hereby incorporated by reference.

Amino acids useful in the present invention may have the carboxyl group at a site other than the terminal carbon atom, the amino group at a site other than the α-position or may be substituted with groups other than oxy, thio, carboxy, amino or guanidino, e.g., cyano, nitro, halo, particularly fluorine, oxo, inorganic acyl groups, etc. Synthetic amino acids may also be monosubstituted on nitrogen as in peptoids, which are oligomers of N-substituted glycine residues. N-substituted amino acids which find use will have an N-substituent of from about 1 to 8 carbon atoms, usually 1 to 6 carbon atoms, which may be aliphatic, alicyclic, aromatic or heterocyclic, usually having not more than about 3 heteroatoms, which may include amino (tertiary or quaternary), oxy, thio, and the like.

Oligopeptides may be constructed by employing standard Merrifield solid phase synthetic methods, manually or by using an automated peptide synthesizer, standard protection chemistry (e.g., t-Boc or Fmoc chemistry) and resins (e.g., 4-methyl benzhydryl amine Rink Amide resin). Successive rounds of deprotection of the terminal amino group and coupling of amino acid monomers, followed by deprotection and cleavage of peptides from resins results in the synthesis of oligopeptides of the desired sequence and length. Additionally, liquid phase peptide synthesis is well known in the art and may also be employed.

If the amino acid monomers employed are N-substituted glycine residues, monomers may incorporate t-butyl-based side chain and 9-fluorenylmethoxycarbonyl α-amine protection. (See, for example, Gordon, et al., J. of Medicinal Chemistry (1994) 37, 1387–1385, and references cited therein.) Controlled oligomerization of the N-substituted monomers may be performed manually and/or robotically with in situ activation by either benzotriazol-1-yloxytris (pyrrolidino)-phosphonium hexafluorophosphate or bromo-tris(pyrrolidino)phosphonium hexafluorophosphate. Additional steps may follow standard automated peptide synthesis protocols using α-(9-fluorenylmethoxycarbonyl) amino acids.

General Connecting Groups ($C_a$ and $C_b$)

Compositions of the invention may include one or more connecting components between the therapeutic or in vitro or in vivo diagnostic agent and the affinity group. The connecting groups may provide for synthetic convenience, particular physical characteristics of the total composition, e.g., water volubility, reduced non-specific binding, lipid solubility, and introduction of markers to allow for better identification of the molecule, e.g. dyes, chromophors, fluorophores and radiolabelled elements inclusive of $C_{14}$ and $H_3$.

For the most part, the connector(s) will be bifunctional, about 1–20 atoms in length, which atoms may be carbon, nitrogen, oxygen, sulfur, phosphorus, and the like. The connector(s) may be alkylene groups, generally of from 2–16, more usually of from 1–25, carbon atoms, polyoxyalkylene groups, where the alkylene groups will be of 2–3 carbon atoms, and having from 1–8, more usually of from about 1–6, units, an amino acid, including alpha and omega amino acids, or oligopeptide having from 1–8, usually 1–6, amino acids, where the amino acids may be polar or nonpolar, charged or uncharged, aliphatic, alicyclic, aromatic or heterocyclic, naturally occurring or synthetic. The connector(s) may also have the structure of an affinity group as described above, thereby providing additional binding affinity at the target site. In a preferred embodiment, Cb is bonded to the reactive group via an ester, thioester, amide, sulfonate ester or sulfonamide linkage. In a further preferred embodiment, Cb is bonded to the O1 amino acid residue in the affinity group via an ester, thioester, amide, sulfonamide, urea, thiourea or carbamate linkage. In a further preferred embodiment, Ca is bonded to E by an ester, thioester, amide, sulfonate ester or sulfonamide linkage. In a further preferred embodiment, Ca is bonded to the reactive group by an ester, thioester, amide or sulfonate ester linkage.

General Entities (E)

In general, the entity may be any moiety that may be linked to the reactive group and will covalently bond to the target molecule. Thus, an entity according to the invention can be any of a wide variety of biologically active or non-biologically active compounds that can bond to targets in a complex mixture. Examples of entities that may be particularly useful in the present invention include in vitro and in vivo diagnostic agents and therapeutic agents.

A. In Vitro Diagnostic Agents

In vitro diagnostic agents find use in in vitro diagnostic analysis. Such in vitro agents include biotin, fluorophors (such as fluorescein), chromophors, radiolabelled probes and chemiluminescent agents and the like, as recognized by those of skill in the art.

B. In Vivo Diagnostic Agents

In another aspect of the invention, the entity may be a compound which allows the diagnostic visualization of specific sites or compartments within the body by employing such diagnostic techniques as positron emission tomography (PET), computerized tomography (CT), single photon emission computerized tomography (SPECT), magnetic resonance imaging (MRI), nuclear magnetic imaging (NMI), fluoroscopy, ultrasound, etc. For such applications, the entity may comprise one or more contrast agents, radioisotopes of such elements as iodine (I), including $^{123}I$, $^{125}I$, $^{131}I$, etc., barium (Ba), gadolinium (Gd), technetium (Tc), including $^{99}Tc$, phosphorus (P), including $^{31}P$, iron (Fe), manganese (Mn), thallium (Tl), chromium (Cr), including $^{51}Cr$, carbon (C), including $^{11}C$, or the like, fluorescently labeled compounds, etc. Such entities are also useful for identifying the presence of particular target sites in a mixture, to label molecules in a mixture, and the like. Various examples are found in U.S. application Ser. No. 08/588,912 assigned to the assignee of this application and hereby incorporated by reference.

C. Therapeutic Agents.

A variety of suitable therapeutic agents are disclosed in U.S. patent application Nos. 08/702,127 and 08/477,900, each of which is hereby incorporated by reference. In this regard, entities are generally less that 10,000 in molecular weight. Entities are such that they perform the desired function in the environment in which they become covalently bonded. For the most part, that environment will be an aqueous environment, usually serum or the interstitium. For use as drugs, the entity may be an agonist, an antagonist, a specific binding compound, an enzyme inhibitor (where the enzyme may be either soluble or membrane bound), a metal chelator, a factor supplement, a molecular scavenger, such as vitamin E, or the like. More specifically, the entity may include thrombin inhibitors, such as argatroban (for example see application Ser. No. 08/674,315 which is hereby incorporated by reference), renin inhibitors, ACE inhibitors, inhibitors of the coagulation and complement cascade, serine proteases, $\alpha_\nu\beta_3$ antagonists, GPIIb/IIIa antagonists, CRF antagonists, or the like.

General Library Synthesis

Combinatorial libraries of affinity groups may be prepared in accordance with conventional ways for producing combinatorial libraries, particularly using a solid support and adding the monomeric components in a stepwise manner. See, for example, U.S. Pat. Nos. 4,883,092; 5,010,175; 5,182,366 and 5,270,170 and PCT applications WO 92/00091; WO 92/09300; WO 93/06121; WO 93/20242; WO 94/06451; WO 94/06291 and WO 95/28640, as exemplary of a much larger literature of techniques. Preferably, the synthetic chemistry is substantially repetitive with the addition of each monomer unit to the growing oligomer.

For purposes of this disclosure, the subject affinity label compounds will be synthesized by conventional methods, although those of ordinary skill will appreciate that other methods may be used. Synthesizers are commercially available for synthesizing oligonucleotides and oligopeptides, as reflected in the references cited above. In addition, various conventional chemistries may be employed. Depending upon the nature of the functional group, the connector and the entity, synthetic strategies will be devised which allow for synthesis of the affinity marker library molecules at reasonable yields and without the formation of complex mixtures. As those of skill will appreciate, the particular synthetic strategy will be determined empirically and on a case by case basis. Methods for combining various compounds are well known in the literature and can be employed with advantage. Where precursors to the entity are known, particularly prodrugs for drugs, the precursor or prodrug will frequently indicate the site for attachment and the nature of a linking group. Where prodrugs are not available, the physiologically active molecule may be modified stepwise at different sites, and the activity of the resulting compound determined.

General Library Screening

Initially, one will have a combinatorial library of compounds having varying oligomeric binding determinants to be screened for their affinity to a target molecule or site. Generally, the compounds will represent at least 50 different affinity groups, frequently 100 different affinity groups, usually at least about 500 different affinity groups, preferably at least about 1000 different affinity groups, and may be 10,000 or more different affinity groups, although usually the libraries will have 5,000 or fewer affinity groups. The library may have greater proportions of one compound over other compounds, but desirably, the relative concentrations will differ by less than about 50%, preferably less than about 25%. For the screening process, the libraries may be divided into smaller units, which will generally range from about 5 to 1,000, frequently from about 5 to 500, usually from about 10 to 500 moieties and more usually from about 10 to 250. During this initial screening process, the library will include a first member of a binding pair (for instance, biotin for the binding pair biotin-avidin), and the first member will be screened with the second member of the binding pair For identification of affinity marker members of the library having particular affinity for a particular target site relative to other members of the library, as indicated previously, depending upon the size of the library, some or all of the members of the library may be combined with the pure target compound in an appropriate reaction medium. The composition of the medium will vary widely, depending upon the nature of the target compound and the environment in which the subject affinity label compounds will be used for bonding to the target compound. For the most part, the media will be polar, particularly aqueous, and may be buffered or otherwise modified to more closely mimic the ultimate environment in which the subject compounds will be used. The concentrations of the target compound and the library members may vary widely, usually being determined empirically, so as to optimize the differentiation between the various members of the library. Generally, for screening purposes, concentrations of the target compound will be in the range of about 0.05 to 5 µM, preferably in the range of about 0.1 to 1.0 µM, while concentrations of the library will vary in the range of about 10 to 150 µM, preferably in the range of from about 50 to 100 µM and more preferably in the range of from about 75 to 85 µM.

The temperature of the reaction may vary broadly as long as it is compatible with the reactants' and media stability. The temperature is thus frequently room temperature or the ambient temperature in which the subject compounds will be used. To the extent that the subject compositions will be used physiologically, the temperature will generally be between about 34–40° C., more usually about 37° C.

The determination of affinity for the target exhibited by the various affinity marker members of the library may be made by determining the composition of the liberated affinity groups at a single time point or a plurality of time points after the reaction is initiated. For the most part, those affinity groups which are liberated the earliest after the reaction is initiated are those which exhibit the greater binding affinity for that target site. Usually, the reaction will be allowed to proceed until there is a sufficient population of liberated affinity groups to allow for their ready determination and differentiation. Preferably, the reaction will be interrupted by the addition of a quenching chemical solution, thus allowing the fastest bonding members only to add to the target protein. In general, reactions terminated by quenching at short reaction times are preferred. Due to the large influence of the quenching solution on the behavior of the screening process, the time when the quenching solution is added will be studied as a separate screening parameter. Quenching times of 1 and 15 minutes will be studied. The affinity label leaving groups may be analyzed by any convenient means, including mass spectrometry, gel electrophoresis, chromatography, e.g., HPLC, TLC, or the like, where, if appropriate, the separated components may then be sequenced. Where a plurality of aliquots of the library used, those sequences demonstrating preferred affinities may then be combined in a subsequent determination for direct comparison.

General Library Screening: Experimental Procedures

The screening of libraries that contain an entity which becomes covalently bonded to the target protein as a result of the affinity labeling reaction described herein may be conducted in two sequential steps and serves as a specific example of a general method for detecting the existence of a covalent adduct. First, a selected target protein reacts with the affinity labeling library or portion thereof. This step is typically conducted at room temperature, although not exclusively so, in the wells of polypropylene 96-well plates. Specified wells contain the target protein typically present at a concentration between 0.1 and 1 µM in a buffered solution of appropriate composition and pH for maintaining the native biological structure and function of the target protein. Labeling reactions are initiated by adding a solution of affinity labeling library members in DMSO to give typical concentrations of total library and DMSO of 80 µM and 2% (volume/volume), respectively. The labeling reactions are terminated at a specified time, as short as 5 seconds or longer than 1 hour, by the addition of a suitable quench reagent (i.e., hydroxylamine for quenching thioesters) that combines with unreacted library members to form other species that do not react with the target protein. As controls, specified wells of the plate contain reaction mixtures that measure the amount of non-covalent binding of the entity to the target protein. These control reactions are conducted by first mixing the library with the quench reagent for a time sufficient to give forms of the library that do not react with the target protein and then adding the target protein.

Second is the detection of the entity that covalently bonds to the target protein, using standard methodologies known in the art, but in a novel time dependent process. For example, if the entity that covalently bonds to the target protein is biotin (or any first binding member of a binding pair), Enzyme-Linked-Immunoassays (ELISA's) can be employed to detect covalent bonding. Briefly, in these assays, polystyrene 96-well plates are coated with an antibody that specifically binds the target protein and modified forms thereof. A portion of each reaction mixture is then transferred to the corresponding wells of the antibody-coated plate, and the binding of target protein to antibody allowed to ensue for approximately 2 hours. The plate is then emptied and 10 times filled with and emptied of phosphate buffered saline (PBS, 10 mM Pi, pH 7.4, 137 mM NaCl, 2.7 mM KCl) to remove non-covalently bound biotin from the well. A solution containing the enzyme conjugate avidin-horse-radish peroxidase (or any second member of a binding pair) may then be added to each washed well, and the binding of avidin of the conjugate to biotin of the modified target molecule, already bound to the antibody of the plate, is complete after 30 minutes. The plate may then be washed as described above; hydrogen peroxide and orthophenyl diamine are added as substrates of the peroxidase enzyme to give a visual measure of the amount of conjugate present in each well; conjugate amount is proportional to the amount of modified target protein in the well. The optical densities of each well are measured, and the values obtained are recorded in a computer spreadsheet and analyzed.

While the ELISA method of screening described above is specific for biotin-containing proteins, the method is, in principle, applicable for measurement of any affinity labeling library that results in the formation of a detectable adduct with any target biomolecule that can be sequestered at the surface of a 96-well plate.

General In Vivo or In Vitro Use of an Identified Affinity Group

Once a particular affinity group is identified, the group may be utilized in vivo for delivery of therapeutic or diagnostic agents or in vitro through coupling to an in vitro diagnostic agent for analysis of molecules to which the affinity group associates.

A. In Vitro

The subject invention thus provides an efficient approach to identifying affinity label compounds that can be used to direct a specific entity to a target site. The subject invention allows for marking specific targets, particularly proteins, for a wide variety of purposes. Where complex mixtures are involved, such as blood, by using the present invention, one can enhance bonding to a specific component in the blood, more particularly, a specific site on the target. In this way, one may achieve specific targeting to mobile components, such as blood cells, e.g., erythrocytes and platelets, proteins, such as immunoglobulins, serum albumin, transferrin, and the like. In mixtures in culture, one may specifically inhibit an enzyme target, so as to prevent enzymatic interference with the culture. For example, one may provide for specific bonding to RNases to prevent degradation of RNA. One may inhibit specific hydrolases, oxidoreductases, or the like. Where one wishes to mark a particular target, one can utilize fluorescent, radioactive, or other entity, which may be detected.

B. In Vivo

When administered physiologically, the targets will usually be proteins, either individually, as aggregates with the same or different proteins or as surface membrane proteins. The subject affinity label compounds, when administered physiologically, will usually be administered as a bolus, but may be introduced slowly over time by transfusion using metered flow, or the like. Alternatively, although less preferable, blood may be removed from the host, contacted with the affinity label compound ex vivo, and returned to the host. The affinity label compounds will be administered in a physiologically acceptable medium, e.g., deionized water, phosphate buffered saline, saline, mannitol, aqueous glucose, alcohol, vegetable oil or the like. Usually, a single injection will be employed, although more than one injection may be used, if desired. The affinity label compounds may be administered by any convenient means, including syringe, catheter or the like. The particular manner of administration will vary depending upon the amount to be administered, whether a single or sequential bolus, or continuous administration, or the like. Administration will be intravascular, where the site of introduction is not critical to this invention, preferably at a site where there is rapid blood flow, e.g., intravenously, peripheral or central vein. The intent is that the compound administered be effectively distributed in the vascular system so as to be able to react with target molecules therein.

The dosage of the affinity label compound will depend upon the entity employed and will, therefore, depend on the adverse effects of the entity, if any, the time necessary to reduce the unbound conch ration of the affinity label compound present in the vascular system, the indication being sought, the sensitivity of the compound to destruction by vascular components, the route of administration and the like. As necessary, the dosage of affinity label compound may be determined empirically, initially using a small multiple of the dosage normally administered, and as greater experience is obtained, enhancing the dosage. Dosages will generally be in the range of 1 ng/kg to 10 mg/kg, usually being determined empirically in accordance with known ways, as provided for in preclinical and clinical studies.

The following examples are offered by way of illustration, and not by way of limitation.

EXAMPLES

In this section, we first describe the construction of S-, O-, and N-linked affinity label libraries: examples 1, 2, and 3 respectively. We then show the results for screening of an S-linked library against HSA at the level of 81 compounds per well (example 4), 9 compounds per well (example 5), and 1 compound per well (example 6). The results of these experiments indicate that -FIYEE (SEQ ID NO:1) is the preferred affinity group for bonding to HSA. Next, results of experiments characterizing the bonding of biotin to HSA using a -FIYEE affinity group (SEQ ID NO:1) are shown. Specifically, example 7 describes methods and materials used for the biological experiments and in examples 8 through 14, we show the results of these experiments.

Example 1

Construction of S-linked Affinity Label Libraries

A representative affinity label library according to the invention and having a p-thiobenzoic acid residue as a reactive group and a thioester bond as a reactive functional group was designed and constructed. The structure of the library is as follows:

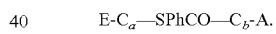

An example of an S-linked library member is Biotin-SPhCO—$O_1$—$O_2$—$X_1$—$X_2$—B—$NH_2$, in which there is no $C_a$.

In the above described structure, $X_1$ and $X_2$ represent that all of the 9 selected L-amino acids appear in a well, $O_1$ represents that only one of the 9 selected L-amino acids appear in a well, $O_2$ represents that only one of the 9 selected D-amino acids appears in a well, and B represents that only one of the 9 selected L-amino acids appears in all 81 wells of a set. Biotin serves as the "entity," as described herein. The "SPhCO" represents a p-thiobenzoyl reactive group R between the biotin "entity" and an oligomeric affinity group ($O_1$—$O_2$—$X_1$—$X_2$—B—$NH_2$).

Biotin is represented by the following structure:

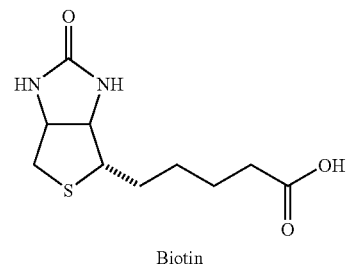

Biotin

Biotinyl is represented by the following structure:

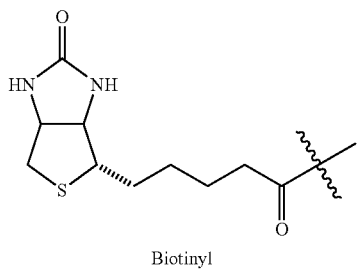

Biotinyl

Thiobenzoyl is represented by the following structure:

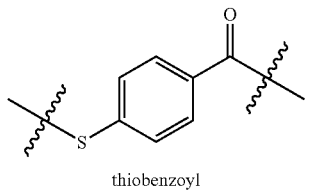

thiobenzoyl

S-9-Fluorenylmethyl p-thiobenzoic acid (Fm—S-Ph-$CO_2H$) is represented by the following structure:

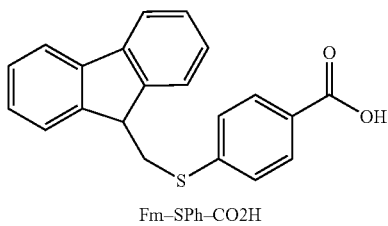

Fm–SPh–CO2H

The precursor for Fm—S-Ph-$CO_2H$, 9-fluorenylmethyl chloride (Fm—Cl), was synthesized as follows. A solution of 25.0 g 9-fluorenylmethanol (127 mmol, Aldrich Chemical) was refluxed with 150 mL thionyl chloride for 30 minutes. The excess thionyl chloride was removed by distillation and the residue distilled at reduced pressure, then crystallized from ethanol two times to afford 19.2 g 9-fluorenylmethyl chloride (89.4 mmol, 70%) as a pale yellow solid.

Fm—S-Ph-$CO_2H$ was prepared as follows: To a 0° C. suspension of 3.40 g 4-mercaptobenzoic acid (85%, Toronto Research Chemicals) (18.7 mmol) in 60 mL N, N-dimethylformamide (DMF) was added 4.00 g 9-fluorenylmethyl chloride (Fm—Cl) (Bodansky, M.; Bednarek, M. A. *Int. J. Pept. Protein Res.* 1982, 20, 434) synthesized as described above, (18.7 mmol) and 6.90 mL diisopropylethylamine (37.4 mmol). The reaction was allowed to slowly warm to RT and then stirred for 16 h. The cloudy yellow-brown solution was washed with hexanes (3×50 mL), diluted with 50 mL 1M HCl and extracted with ethylacetate (3×50 mL), washed with 50 mL sat. aq. NaCl, dried with anhyd. $MgSO_4$, filtered, and concentrated via rotary evaporation to afford a yellow-brown oil. This oil was then dissolved in 20 mL MeOH, cooled to −20° C. and the resulting crystals were collected by filtration, washed with ice cold MeOH and dried to afford 5.59 g of Fm—S-Ph-$CO_2H$ as a white solid (13.0 mmol, 70%).

The nine amino acids employed were carefully selected by considerations of the side chain functional groups and are listed in Table 1.

TABLE 1

| Code | Amino Acid | Category | Starting Material |
| --- | --- | --- | --- |
| 1 | glutamic acid | acid | Fmoc-Glu(OtBu)-OH |
| 2 | glutamine | amide | Fmoc-Gln(Trt)-OH |
| 3 | arginine | base | Fmoc-Arg(Pmc)-OH |
| 4 | methionine | sulfide | Fmoc-Met-OH |
| 5 | serine | alcohol | Fmoc-Ser(tBu)-OH |
| 6 | tyrosine | phenol | Fmoc-Tyr(tBu)-OH |
| 7 | leucine | aliphatic | Fmoc-Leu-OH |
| 8 | phenylalanine | aromatic | Fmoc-Phe-OH |
| 9 | tryptophan | aromatic | Fmoc-Trp(Boc)-OH |

The D-amino acids, $O_2$, were introduced in order to prevent facile peptidyl cleavage in vivo and to maximize the affinity to the macromolecular targets.

In each set, there are 81 wells and in each well, there are 81 compounds while B is fixed. Such results in a library of 6561 total library members.

For example, when glutamic acid (E) was chosen to be the residue "B" in the above formula, the set 1 of combinatorial p-thiobenzoyl-containing affinity labeling libraries Biotin-SPhCO—$O_1$—$O_2$—$X_1$—$X_2$-E-$NH_2$ was constructed as follows:

The synthesis utilized Merrifield solid phase peptide synthesis methods and Fmoc chemistry. Rink amide MBHA resin was used to furnish amide at the C-terminus.

A schematic illustration outlining the construction of this set of libraries described above is shown in FIG. 3.

Figure 3:
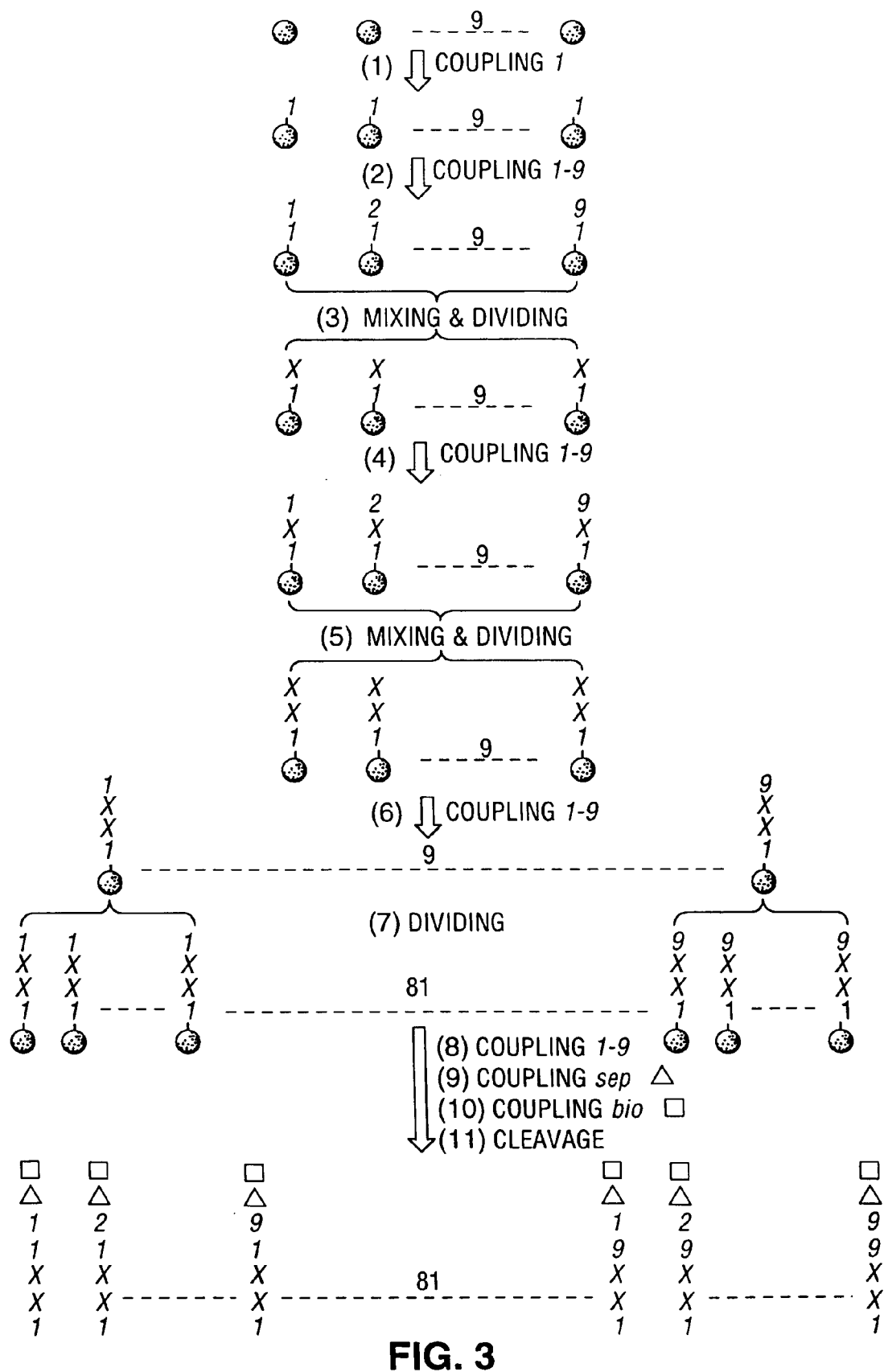
FIG. 3 shows a schematic illustration of the construction of an affinity labeling library of the present invention.

In step (1) shown in FIG. 3, Fmoc-Glu(OtBu)-OH was coupled to an identical amount of resin support in all 9 reaction vessels after removal of the Fmoc protecting group on Rink amide MBHA resin.

Removal of the Fmoc group was performed by treating with 20% piperidine in N-methylpyrrolidinone (NMP) twice, 2 minutes and 15 minutes, respectively at room temperature, followed by several NMP washes.

Coupling of the Fmoc-Glu(OtBu)-OH to the resin support was performed by adding to the resin in a reaction vessel with an N,N-dimethylformamide (DMF) solution of the amino acid (4 equivalents), o-benzotriazol-1-yl-N,N,N',N'-tetramethyl-uronium hexafluorophosphate (HBTU) (4 equivalents), 1-hydroxybenzotriazole (HOBt) (4 equivalents) and diisopropylethyl amine (DIEA) (8 equivalents). The reactions were allowed to proceed for 2 hours at room temperature. Completion of each reaction was monitored by a ninhydrin test to detect the presence of unreacted amino groups. The coupling reactions were repeated until the ninhydrin test for each reaction was negative. Once coupling was complete, as evidenced by a negative ninhydrin test, the peptide resin in each of the nine separate reactions was washed repeatedly with DMF.

Before the second L-amino acids were coupled to an identical amount of resin bearing the same Fmoc protected amino acid (i.e., Fmoc-Glu(OtBu)-OH) in all 9 reaction vessels), the Fmoc protecting group was removed by treating with 20% piperidine in NMP twice, 2 minutes and 15 minutes, respectively, at room temperature, followed by several NMP washes.

As shown in step (2) of FIG. 3, each of the nine different Fmoc-protected L-amino acids shown in Table 1 were then individually linked to an identical amount of resin in all 9 reaction vessels. Coupling reactions were again carried out by adding to the resin in a reaction vessel with a DMF solution of the amino acid (4 equivalents), HBTU (4 equivalents), HOBt (4 equivalents) and DIEA (8 equivalents). The reactions were allowed to proceed for 2 hours at room temperature. Completion of each reaction was monitored by a ninhydrin test. The coupling reactions were repeated until the ninhydrin test for each reaction was negative. Once coupling was complete as evidenced by negative ninhydrin test, the peptidyl resin in each of the nine separate reactions was washed with DMF.

The result of this second round of coupling is the generation of nine equimolar independent and distinct pools of dipeptides linked to resin support. As shown in FIG. 3, since each of the nine independent and distinct pools contains one distinct dipeptide, there are now 9 distinct dipeptides generated.

As shown in step (3) of FIG. 3, the resins from each of the nine independent and distinct pools generated in step (2) were mixed and then divided into identical pools. This gives rise to nine identical pools, each consisting of nine distinct dipeptides linked to the resin support.

Before the third round of coupling, the Fmoc protecting group was removed by treating with 20% piperidine in NMP twice, 2 minutes and 15 minutes, respectively, at room temperature, followed by several NMP washes.

As shown in step (4) of FIG. 3, each of the nine different Fmoc-protected L-amino acids shown in Table 1 were individually linked to an identical pool of resin in all nine reaction vessels. Coupling reactions were carried out as described above.

As shown in step (5) of FIG. 3, the resins from each of the nine independent and distinct pools generated in step (4) were mixed and then divided into identical pools, producing nine identical pools, each consisting of 81 distinct tripeptides linked to the resin support.

Before the fourth round of coupling, the Fmoc protecting group was removed by treating with 20% piperidine in NMP twice, 2 minutes and 15 minutes, respectively at room temperature, followed by several NMP washes.

As shown in step (6) of FIG. 3, each of the nine different Fmoc-protected amino acids shown in Table 1 were linked to an identical pool of resin in all nine reaction vessels. In this round of coupling, unlike any of the other round of coupling, amino acids in the D-configuration are employed. Coupling reactions were again carried out as described above.

This fourth round of coupling generates nine equimolar independent and distinct pools of tetrapeptides linked to resin support. As shown in FIG. 3, since each of the nine independent and distinct pools contains 81 distinct tetrapeptides, there are now 729 distinct tetrapeptides generated.

As shown in step (7) of FIG. 3, each of the nine independent and distinct pools of tetrapeptides generated in step (6) were each divided into a set of nine identical pools without mixing the pools before dividing, giving rise to nine sets of identical pools (81 pools total), each pool containing 81 tetrapeptides. The step of splitting the pools without mixing permits the fourth and fifth amino acids coupled to the resin to be defined. Before the fifth round of coupling, the Fmoc protecting group was removed by treating with 20% piperidine in NMP twice, 2 minutes and 15 minutes, respectively, at room temperature, followed by several NMP washes.

As shown in step (8) of FIG. 3, each of the nine identical pools in each of the nine sets of pools generated in step (7) was then coupled by one of the nine Fmoc-protected amino acids shown in Table 1. Coupling reactions were again carried out as described above.

This fifth round of coupling generates eighty-one equimolar independent and distinct pools of pentapeptides linked to a resin support. As shown in FIG. 3, since each of eighty-one independent and distinct pools contains eighty-one distinct pentapeptides, 6561 distinct pentapeptides have been generated.

As shown in step (9) of FIG. 3, each of the eighty-one independent and distinct pools generated in step (8) was then coupled to S-9-fluorenylmethyl-p-thiobenzoic acid (Fm—S—Ph-CO$_2$H). Before the coupling of Fm—S-Ph-CO$_2$H, the Fmoc protecting group was removed by treating with 20% piperidine in NMP twice, 2 minutes and 15 minutes, respectively at room temperature, followed by several NMP washes.

Coupling reactions were carried out by adding to the resin in a reaction vessel with a DMF solution of S-9-fluorenylmethyl-p-thiobenzoic acid (4 equivalents), HBTU (4 equivalents), HOBt (4 equivalents) and DIEA (8 equivalents). The reactions were allowed to proceed for 2 hours at room temperature. Completion of each reaction was monitored by a ninhydrin test. The coupling reactions were repeated until the ninhydrin test for each reaction was negative. Once coupling was complete as evidenced by a negative ninhydrin test, the peptidyl resin in each of the nine separate reactions was washed with DMF.

Before the last round of coupling, the fluorenylmethyl protecting group was removed by treating with 20% piperidine in NMP twice, 2 minutes and 10 minutes, respectively at room temperature, followed by NMP washes rapidly.

As shown in step (10) of FIG. 3, each of eighty-one independent and distinct pools generated in step (8) was then coupled to biotin. Coupling reactions were carried out by adding to the resin in a reaction vessel with a DMF solution of biotin (5 equivalents), HBTU (5 equivalents), HOBt (5 equivalents) and DIEA (10 equivalents). The reactions were allowed to proceed for 2 hours at room temperature. The coupling reactions were repeated to ensure completion.

Finally, to complete the construction of the p-thiobenzoyl-containing affinity labeling libraries, as shown in step (11) of FIG. 3, the completely constructed affinity labeling libraries were cleaved from the resin component and cleavage and purification were performed as follows.

The peptidyl resin mixtures in each 81 independent and distinct pools generated in step (10) were dried and then independently treated with trifluoroacetic acid (TFA)/H$_2$O (95/5, v/v) for 1.5 hours. The peptide/TFA solutions were then precipitated then washed with ether. Following ether precipitation, the peptide solutions were suspended in 0.045% TFA in water and lyophilized, to yield the completely constructed and dried p-thiobenzoyl-containing affinity labeling library.

The final combinatorial p-thiobenzoic-containing affinity labeling library is substantially stable under normal storage conditions as determined by mass spectral analysis.

Example 2

Construction of O-Linked Affinity Labeling Libraries

In addition to S-linked libraries, O-linked libraries can be synthesized having a p-hydroxybenzoic acid as a reactive functional group. Individual solid phase peptide synthesis is performed on an Applied Biosystems 433A Peptide Synthesizer using FastMoc Chemistry. Multiple peptide syntheses are performed on a Gilson AMS 422 Multiple Peptide Synthesizer using Fmoc chemistry. Solid phase reactions were monitored by ninhydrin test for completion. Amino acids and Rink Amide MBHA resin were obtained from NovaBiochem. Preparative HPLC was performed on a 21.4×250 mm $C_{18}$ reverse phase column using 5–60% B (0.045% TFA in $H_2O$ and 0.045% TFA in $CH_3CN$) gradient elution. Liquid Chromatography/Mass Spectrometry results were obtained using electrospray ionization on a Perkin Elmer Sciex API300 Mass Spectrometer using a 1.0×250 mm $C_{18}$ reverse phase protein/peptide column using 0–70% B (0.045% TFA in $H_2O$ and 0.045% TFA in $CH_3CN$) gradient elution.

The structure of p-hydroxybenzoyl is as follows:

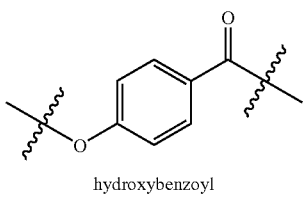

hydroxybenzoyl

The structure of Fmoc-OPh-$CO_2H$ is as follows:

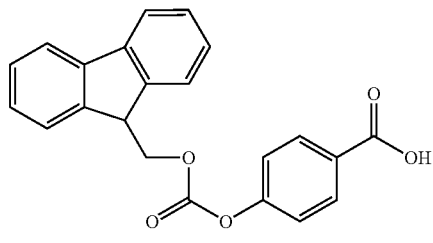

Fmoc–OPh–CO2H

Synthesis of 9 Individual Library Members

Synthesis was performed on the Gilson AMS 422 Multiple Peptide Synthesizer using 25 µmol Rink amide MBHA resin/reaction tube. Deprotection of the Rink amide MBHA resin and subsequent deprotections of the Fmoc amino acids were carried out using 25% piperidine in N,N-dimethylformamide (DMF) (4×5 min each) followed by a DMF wash (6 times). Coupling of the amino acids, each dissolved in N-methylpyrrolidinone (NMP), was performed two using 300 µL of 0.68 M amino acid solution (8 eq) in N-methylpyrrolidinone (NMP), 440 µL of 0.45 M solution of o-benzotriazol-1-yl-N,N,N',N'-tetramethyl-uronium hexafluorophosphate (HBTU) and 1-hydroxybenzotriazole (HOBt) (8 eq) in DMF, and 100 µL of 4 M N-methylmorpholine (NMM) (16 eq) in DMF were added and allowed to react for 1 h. Upon completion, dichloromethane (DCM) was added and reaction continued for 1 h. The reaction mixtures were then filtered and washed with DMF (6 times) and the next amino acid coupling was performed. The first coupling reaction was Glu, the second was one of nine different amino acids (Glu, Gln, Arg, Met, Ser, Tyr, Leu, Phe, and Trp), one amino acid/tube, the third coupling was Tyr, followed by D-Leu, then Phe.

The addition of the O-Ph group was performed in exactly the same way as an amino acid coupling. First, the last amino acid added was deprotected and washed, then 300 µL of 0.68 M Fmoc-O-Ph-$CO_2H$ (8 eq) in DMF, 440 µL of a 0.45 M solution HBTU/HOBt (8 eq) in DMF, and 100 µL of 4 M NMP (16 eq) in DMF were added and allowed to react for 1 h. Then, DCM was added and reaction continued for 1 h, followed by the removal of the Fmoc group with 25% piperidine in DMF.

Biotin was added by reacting 980 µL of a 128 mM biotin isobutyl carbonic anhydride (5 eq) solution (2×10 h each). The resins were then washed with DMF (6 times) and DCM (6 times).

Each of the peptidyl resin mixtures was then independently treated with 0.75 mL trifluoroacetic acid (TFA):$H_2O$: phenol (10:0.5:0.75, v/v/wt) (2×1 h each), washed with 0.75 mL TFA and 0.75 mL DCM. The combined filtrates were then concentrated via speed vac and products isolated by precipitation with dry-ice cold $Et_2O$ (3 mL) followed by centrifugation. The resulting white solids were then washed with dry-ice cold $Et_2O$ (2×3 mL each), then dissolved in 1.5 mL of 0.045% TFA in $H_2O$ and 1.5 mL of 0.045% TFA in $CH_3CN$, allowed to stand at RT for 1 h then purified by reverse phase prep HPLC to afford the products, after lyophylization, as white solids.

Synthesis of Biotin Isobutyl Carbonic Anhydride

In a 50-mL round-bottomed flask equipped with a magnetic stir bar and $N_2$ inlet adapter was dissolved 822 mg biotin (3.30 mmol) in 23.9 mL hot DMF. After cooling to room temperature, 1.38 mL triethylamine (9.90 mmol) was added followed immediately by 428 µL isobutylchloroformate (3.30 mmol). Immediately, a precipitate formed and the reaction was allowed to stir at RT for 10 min. The insoluble precipitate (TEA.HCl) was removed by filtration to afford the approximately 128 mM biotin isobutyl carbonic anhydride solution.

Example 3

Construction of N-Linked Affinity Labeling Libraries

In addition to S-linked and O-linked libraries, N-linked libraries can be synthesized having a p-aminobenzoic acid as a functional group. Individual solid phase peptide syntheses can be performed on an Applied Biosystems 433A Peptide Synthesizer using FastMoc Chemistry. Multiple peptide syntheses can be performed on a Gilson AMS 422 Multiple Peptide Synthesizer using Fmoc chemistry. Solid phase reactions can be monitored by ninhydrin test for completion. Amino acids and Rink Amide MBHA resin can be obtained from NovaBiochem. Preparative HPLC can be performed on a 21.4×250 mm $C_{18}$ reverse phase column using 5–60% B (0.045% TFA in $H_2O$ and 0.045% TFA in $CH_3CN$) gradient elution. Liquid Chromatography/Mass Spectrometry analysis can be obtained using electrospray ionization on a Perkin Elmer Sciex API300 Mass Spectrometer using a 1.0×250 mm $C_{18}$ reverse phase protein/peptide column using 0–70% B (0.045% TFA in $H_2O$ and 0.045% TFA in $CH_3CN$) gradient elution.

The structure of p-aminobenzoyl is as follows:

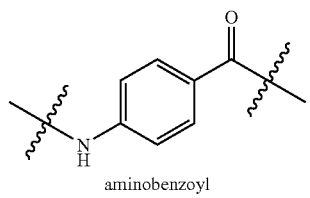

aminobenzoyl

The structure of Fmoc-HNPh-CO₂H is as follows:

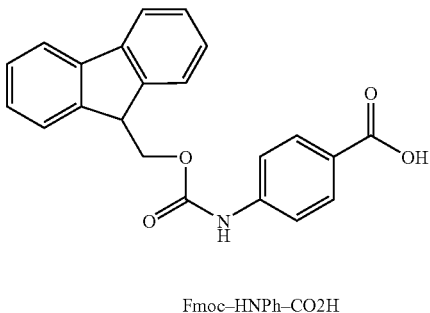

Fmoc–HNPh–CO2H

Synthesis of 9 Individual Library Members

Synthesis can be performed on the Gilson AMS 422 Multiple Peptide Synthesizer using 25 μmol Rink amide MBHA resin/reaction tube. Deprotection of the Rink amide MBHA resin and subsequent deprotections of the Fmoc amino acids can be carried out using 25% piperidine in N,N-dimethylformamide (DMF) (4×5 min each) followed by a DMF wash (6 times). Coupling of the amino acids, each dissolved in N-methylpyrrolidinone (NMP), can be performed two using 300 μL of 0.68 M amino acid solution (8 eq) in NMP, 440 μL of 0.45 M solution of o-benzotriazol-1-yl-N,N, N,N'-tetramethyl-uronium hexafluorophosphate (HBTU) and 1-hydroxybenzotriazole (HOBt) (8 eq) in DMF, and 100 μL of 4 M N-methylmorpholine (NMM) (16 eq) in DMF are then added and allowed to react for 1 h. Upon completion, dichloromethane (DCM) was added and the reaction continued for 1 h. The reaction mixtures are then filtered and washed with DMF (6 times) and the next amino acid coupling was performed. The first coupling reaction can be Glu, the second was one of nine different amino acids (Glu, Gln, Arg, Met, Ser, Tyr, Leu, Phe, and Trp), one amino acid/tube, the third coupling was Tyr, followed by D-Leu, then Phe.

The addition of the N-Ph group can be performed in exactly the same way as an amino acid coupling. First, the last amino acid added is deprotected and washed, then 300 μL of 0.68 M Fmoc-NH-Ph-CO₂H—S-Ph-CO₂H (8 eq) in DMF, 440 μL of 0.45 M solution HBTU/HOBt (8 eq) in DMF, and 100 μL of 4 M NMP (16 eq) in DMF are added and allowed to react for 1 h. Upon completion, DCM is added and reaction continued for 1 h, followed by the removal of the Fmoc group with 25% piperidine in DMF.

Biotin is added by reacting 980 μL of a 128 mM biotin carbonic anhydride (5 eq) solution (2×10 h each). The resins are then washed with DMF (6 times) and DCM (6 times).

Each of the peptidyl resin mixtures can then independently treated with 0.75 mL trifluoroacetic acid (TFA):H₂O: phenol (10:0.5:0.75, v/v/wt) (2×1 h each), washed with 0.75 mL TFA and 0.75 mL DCM. The combined filtrates are then concentrated via speed vac and products isolated by precipitation with dry-ice cold Et₂O (3 mL) followed by centrifugation. The resulting white solids are then washed with dry-ice cold Et₂O (2×3 mL each), then dissolved in 1.5 mL of 0.045% TFA in H₂O and 1.5 mL of 0.045% TFA in CH₃CN, allowed to stand at RT for 1 h then purified by reverse phase prep HPLC to afford the products, after lyophylization, as white solids.

Synthesis of Individual Compounds

Biotin Isobutylcarbonic Anhydride Solution

In a 10-mL round-bottomed flask equipped with a magnetic stir bar and N₂ inlet adapter was dissolved 300 mg of biotin (1.23 mmol) in 5 mL of hot DMF. This was allowed to cool to RT where 677 μL of triethylamine (4.86 mmol) was added followed immediately by 160 μL of isobutylchloroformate (1.23 mmol). Immediately, a precipitate formed and the reaction was allowed to stir at RT for 10 min. The insoluble precipitate (TEA.HCl) was removed by filtration and washed with 2-mL of DMF to afford 8 mL of the approximately 154 mM biotin carbonic anhydride solution containing approximately 453 mM TEA (3.63 mmol).

Synthesis of Biotin-OPh-CO-FIYEE-NH₂

Figure 16:
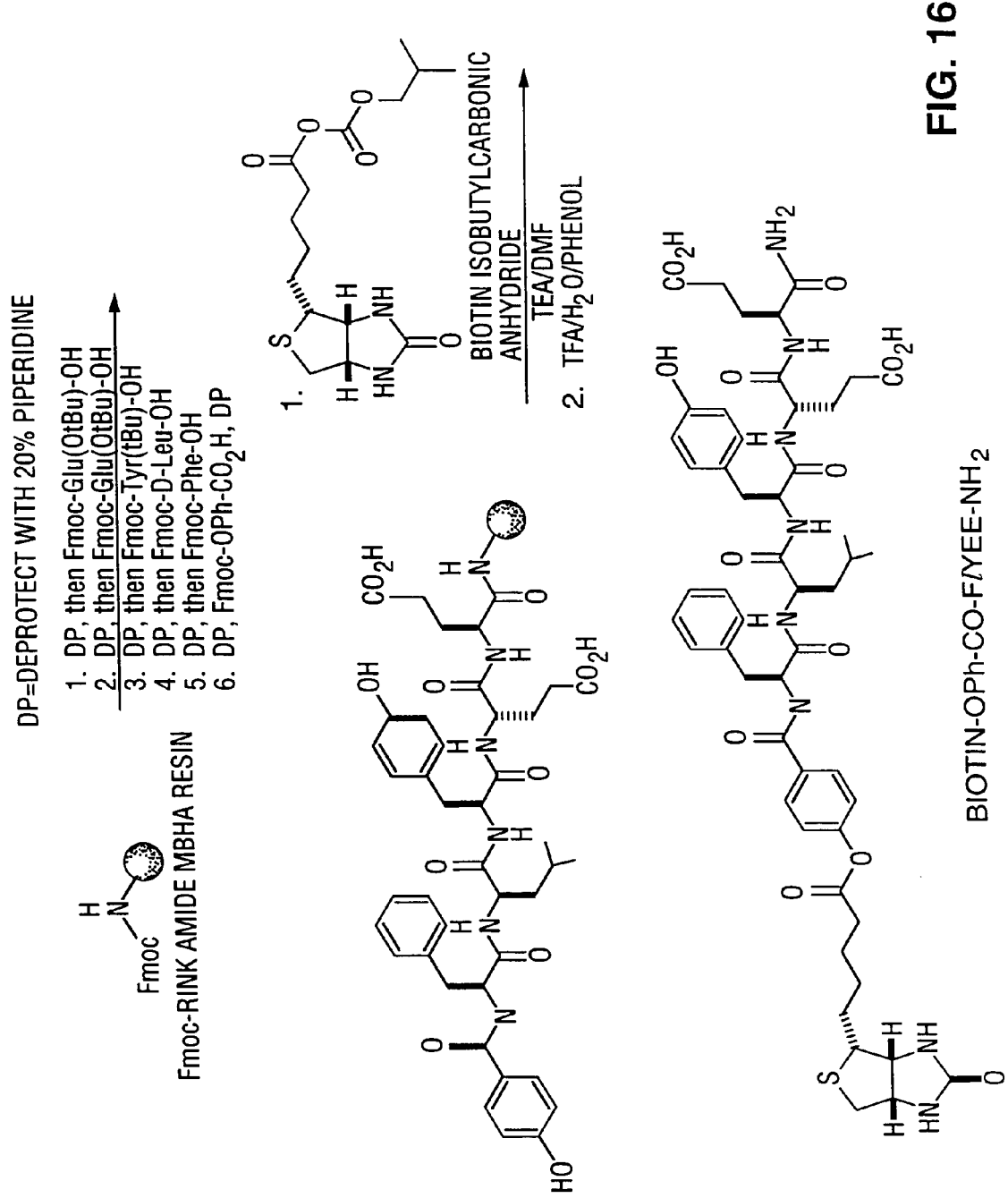
FIG. 16 is a reaction scheme setting forth the procedure for the synthesis of biotin-OPh-CO-FIYEE-NH$_2$ according to the invention.

The procedure followed for this synthesis is illustrated schematically in FIG. 16. Synthesis of the fragment HO-Ph-CO-FIYEE-PS was synthesized using Applied Biosystems 433A peptide synthesizer using FastMoc chemistry (HBTU/HOBt/DIEA) with final deprotection on a 0.250 mmol scale using Fmoc-Rink amide MBHA resin (NovaBiochem) in 98% yield. The resulting fragment was then transferred to a 20-mL glass solid phase reaction vessel and washed with three 4-mL portions of DMF. This was then shaken with 8 mL of an approximately 150 mM solution of biotin isobutylcarbonic anhydride solution (1.23 mmol) with approximately 453 mM TEA (3.63 mmol) for 70 h. This was then filtered and washed with six 4-mL portions of DMF and three 4-mL portions of DCM. The resin was then treated with two 4-mL portions of cleavage cocktail solution (10 mL TFA, 0.5 mL water and 0.75 g phenol) for 1 h each. The resin was then washed with 4 mL TFA and 4 mL DCM and the combined cleavage and washing filtrates were concentrated by rotary evaporation to 2 mL. The crude product was then isolated by precipitation with 30 mL dry-ice cold Et₂O followed by centrifugation. After decanting the supernatant, the resulting white solid was re-suspended in 30 mL dry-ice cold ether, centrifuged, and decanted two times. This was then dissolved in 10 mL of 0.045% TFA in CH₃CN and 10 mL of 0.045% TFA in water, allowed to stand at RT for 1 h, frozen and lyophilized to afford 219 mg of the crude product as a white solid. Analytical HPLC reveals product to be approximately 80% pure (contains approximately 10% HO-Ph-CO-FIYEE-NH₂). This was then purified by preparative reverse-phase HPLC to afford 121 mg of biotin-OPh-CO-FIYEE-NH₂ as a white solid (0.115 mmol, 47%). $^1$H NMR (500 MHz, DMSO-d₆) δ 12.05 (br s, 2H), 9.06 (br s, 1H), 8.57 (d, J=8.0 Hz, 1H), 8.19–8.17 (m, 3H), 7.84–7.81 (m, 3H), 7.32 (d, J=7.4 Hz, 1H), 7.28 (br s, 1H), 7.24 (t, J=7.5 Hz, 2H), 7.17 (d, J=8.7 Hz, 2H), 7.14 (d, J=7.2 Hz, 1H), 7.07 (brs, 1H), 7.00 (m, 3H), 6.58 (d, J=8.4 Hz, 2H), 6.44 (br s, 1H), 6.35 (br s, 1H), 4.73–4.70 (m, 1H), 4.47–4.43 (m, 1H), 4.334.30 (m, 1H), 4.304.20 (m, 2H), 4.204.14 (m, 2H), 3.16–3.12 (m, 1H), 3.04 (dd, J=13.5, 5.0 Hz, 1H), 2.97–2.93 (m, 2H), 2.83 (dd, J=12.5, 5.0 Hz, 1H), 2.64–2.54 (m, 4H), 2.30–2.24 (m, 2H), 2.20 (t, J=8.0 Hz, 2H), 1.95–1.85 (m, 2H), 1.85–1.76 (m, 1H), 1.76–1.70 (m, 1H), 1.70–1.60 (m, 3H), 1.56–1.42 (m, 1H), 1.42–1.35 (m, 2H), 1.16–1.12 (m, 3H), 0.71 (d, J=6.0 Hz, 3H), 0.69 (d, J=6.0 Hz, 3H). Anal. HPLC indicated product to be >95% pure with $R_t$=48.34 min. ESI-MS m/z for $C_{51}H_{65}N_8O_{14}S$ (MH⁺), calcd 1045.4, found 1045.8.

N-Tritylglycine Isobutylcarbonic Anhydride Solution

In a 10-mL round-bottomed flask equipped with a magnetic stir bar and N₂ inlet adapter was dissolved 333 mg N-trityl glycine (Aldrich) (1.05 mmol) in 2 mL DCM. To this was added 558 μL triethylamine (4.86 mmol) was added followed immediately by 130 μL isobutylchloroformate (1.23 mmol). Immediately, a precipitate formed and the reaction was allowed to stir at RT for 5 min. The insoluble precipitate (TEA.HCl) was removed by filtration and washed with 2 mL DCM to afford approximately 5 mL of the approximately 200 mM N-tritylglycine isobutylcarbonic anhydride solution containing approximately 600 mM TEA (3.00 mmol).

Synthesis of Biotin-Gly-OPh-CO-FIYEE-NH$_2$

Figure 17:
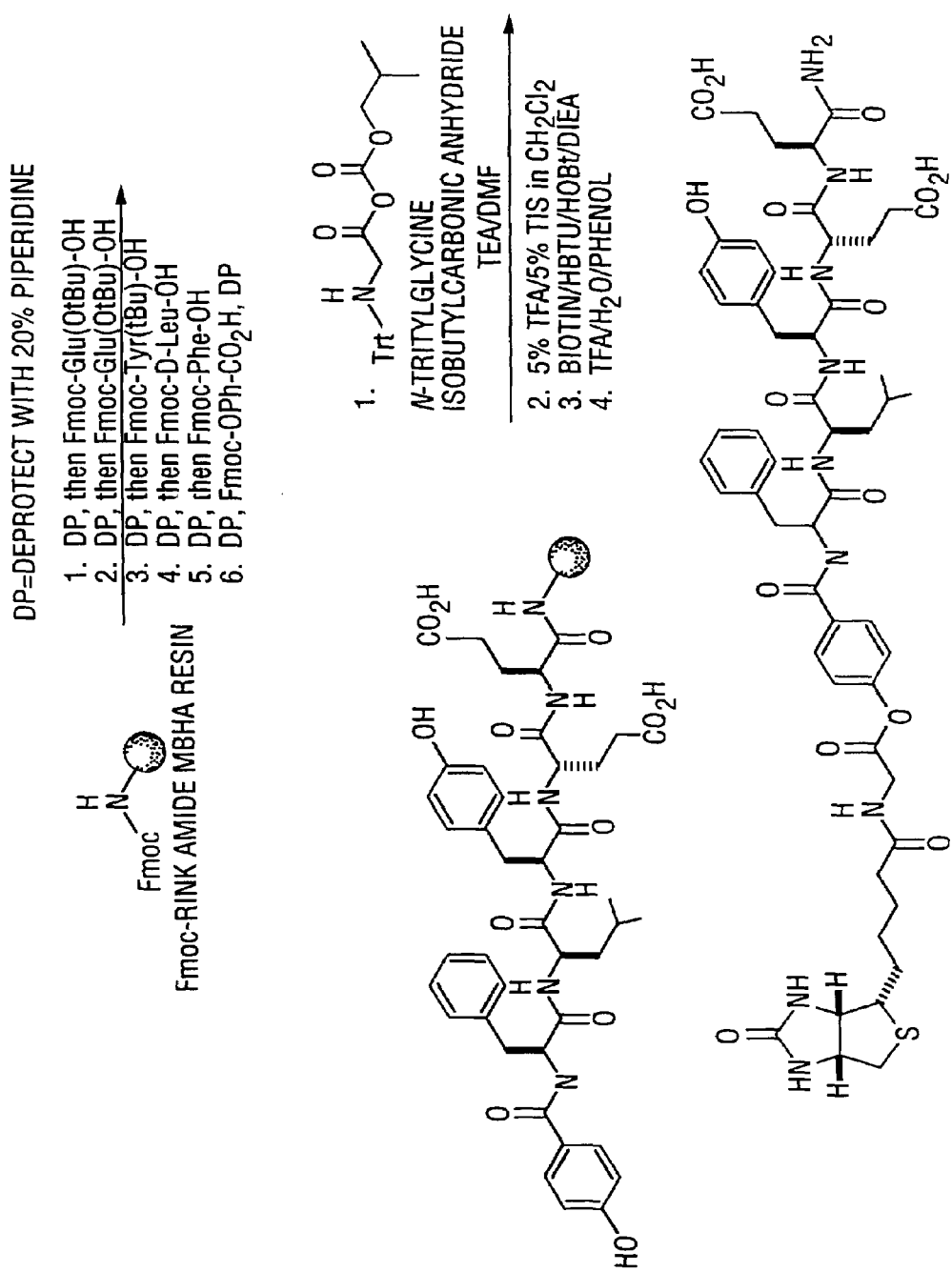
FIG. 17 is a reaction scheme setting forth the procedure for the synthesis of biotin-Gly-OPh-CO-FIYEE-NH$_2$ according to the invention.

The procedure for this synthesis is illustrated schematically in FIG. 17. Synthesis of the fragment HO-Ph-CO-FIYEE-PS was synthesized using Applied Biosystems 433A peptide synthesizer using FastMoc chemistry (HBTU/HOBt/DIEA) with final deprotection on a 0.250 mmol scale using Fmoc-Rink amide MBHA resin (NovaBiochem) in 98% yield. A 354 mg portion of the resulting fragment was then transferred to an 8-mL solid phase reaction vessel and washed with three 4-mL portions of DCM. This was then shaken with 5 mL of an approximately 200 mM solution of N-tritylglycine isobutylcarbonic anhydride solution (1.23 mmol) with approximately 600 mM TEA (3.63 mmol) for 24 h. This was then filtered and washed with six 2-mL portions of DCM, then treated with five 2-mL portions of (100:5:5) DCM/TFA/TIS (dichloromethane/trifluoroacetic acid/triisopropylsilane) for 2 min each and washed with six 2-mL portions of DCM, three 2-mL portions of DMF, 2 mL of 2 M DIEA in NMP and three 2-mL portions of DMF to afford a pale tan resin. This was then shaken with a solution of 122 mg biotin (0.500 mmol) in 1.10 mL of 0.45 M HBTU/HOBt in DMF, 250 µL of 2 M DIEA in NMP, and 1.10 mL DMF (heat was required for dissolution) for 1 h. The resin was then filtered and washed with six 2-mL portions of DMF and three 2-mL portions of DCM. The resin was then treated with two 2-mL portions of cleavage cocktail solution (10 mL TFA, 0.5 mL water and 0.75 g phenol) for 1.5 h each. The resin was then washed with 2 mL TFA and 2 mL DCM and the combined cleavage and washing filtrates concentrated by rotary evaporation to 2 mL. The crude product was then isolated by precipitation with 40 mL dry-ice cold Et$_2$O followed by centrifugation. After decanting the supernatant, the resulting white solid was re-suspended in 40 mL dry-ice cold ether, centrifuged, and decanted two times. This was then dissolved in 6 mL of 0.045% TFA in CH$_3$CN and 6 mL of 0.045% TFA in water, allowed to stand at RT for 1 h, frozen and lyophilized to afford the crude product as a white solid. This was then purified by preparative reverse-phase HPLC to afford 29.4 mg of biotin-Gly-OPh-CO-FIYEE-NH$_2$ as a white solid (0.027 mmol, 21%). Anal. HPLC indicated product to be >95% pure with R$_t$=45.43 min. ESI-MS m/z for C$_{53}$H$_{68}$N$_9$O$_{15}$S (MH$^+$), calcd 1102.5, found 1103.0.

LC-Biotin Isobutylcarbonic Anhydride Solution

In a 10-mL round-bottomed flask equipped with a magnetic stir bar and N$_2$ inlet adapter was dissolved 108 mg of N-(+)-biotin-6-aminocaproic acid (0.302 mmol) in 6 mL of hot DMF. This was allowed to cool to RT where 167 µL of triethylamine (1.20 mmol) was added followed immediately by 39.2 µL of isobutylchloroformate (0.302 mmol). The reaction was then allowed to stir at RT for 10 min to afford approximately 6.2 mL of the approximately 50 mM LC-biotin isobutylcarbonic anhydride solution containing approximately 145 mM TEA (0.898 mmol).

Synthesis of LC-Biotin-OPh-CO-FIYEE-NH$_2$

Figure 18:
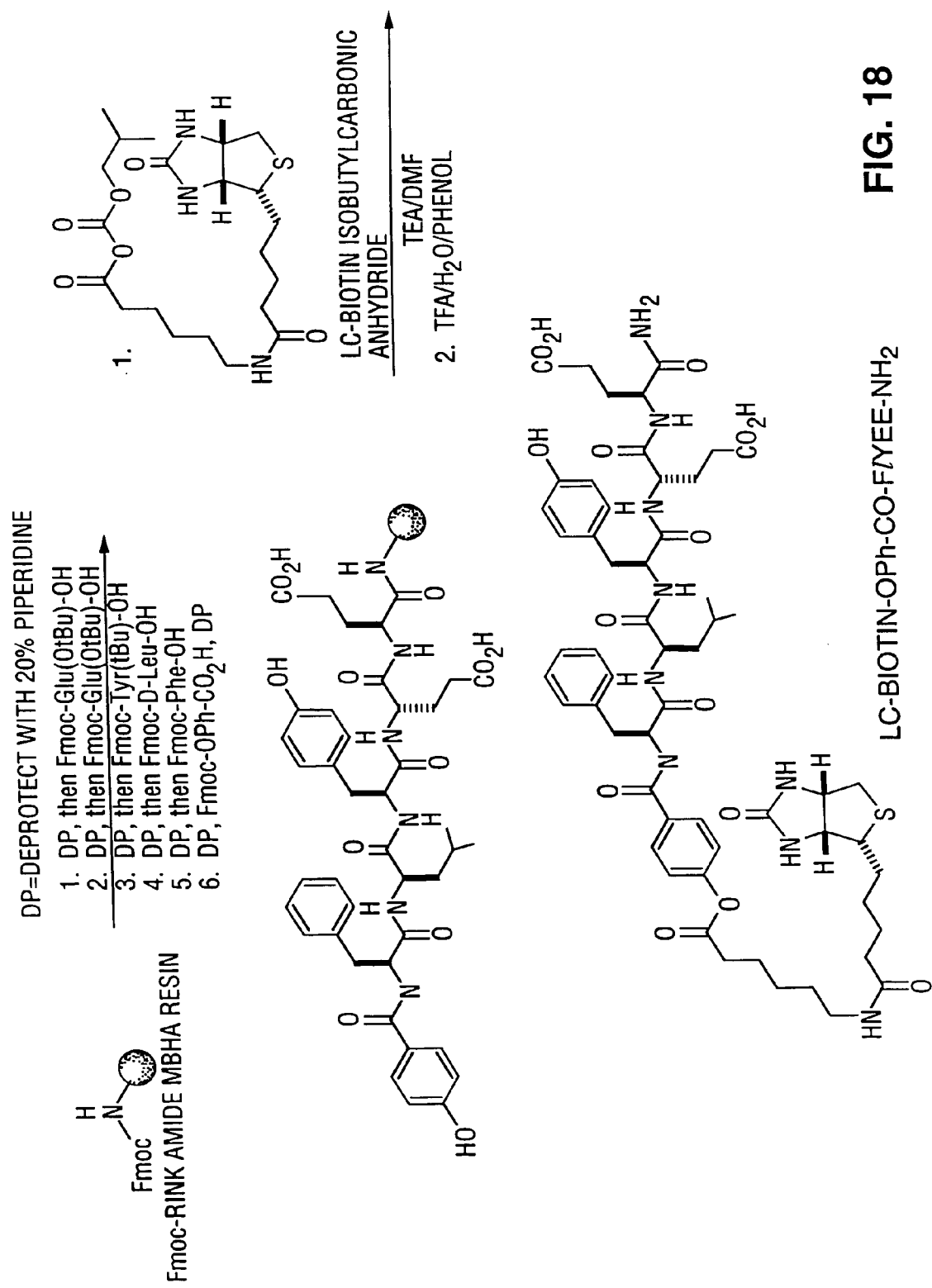
FIG. 18 is a reaction scheme setting forth the procedure for the synthesis of LC-biotin-OPh-CO-FIYEE-NH$_2$ according to the invention.

The procedure followed for this synthesis is illustrated schematically in FIG. 18. Synthesis of the fragment HO-Ph-CO-FIYEE-PS (PS is polystyrene) was synthesized using Applied Biosystems 433A peptide synthesizer using FastMoc chemistry (HBTU/HOBt/DIEA) with final deprotection on a 0.250 mmol scale using Fmoc-Rink amide MBHA resin (NovaBiochem) in 98% yield. A 0.120 mmol portion of the resulting fragment was then transferred to an 8-mL solid phase reaction vessel and washed with three 4-mL portions of DMF. This was then shaken with approximately 6.2 mL of approximately 50 mM solution of LC-biotin isobutylcarbonic anhydride solution (0.302 mmol) with approximately 145 mM TEA (0.898 mmol) for 21 h. This was then filtered and washed with six 2-mL portions of DMF and three 4-mL portions of DCM. The resin was then treated with two 1.5-mL portions of cleavage cocktail solution (10 mL TFA and 0.5 mL water) for 1.25 h each. The resin was then washed with 2 mL TFA and 2 mL DCM and the combined cleavage and washing filtrates were concentrated by rotary evaporation to 1.5 mL. The crude product was then isolated by precipitation with 13 mL dry-ice cold Et$_2$O followed by centrifugation. After decanting the supernatant, the resulting white solid was re-suspended in 13 mL dry-ice cold ether, centrifuged, and decanted two times, then dried to afford 98.1 mg of a white solid. Analytical HPLC reveals product to be approximately 52% pure (contains approximately 48% HO-Ph-CO-FIYEE-NH$_2$). This was then dissolved in 4 mL of 0.045% TFA in CH$_3$CN and 4 mL of 0.045% TFA in water and purified by preparative reverse-phase HPLC to afford 47.2 mg of LC-biotin-OPh-CO-FIYEE-NH$_2$ as a white solid (0.041 mmol, 34%). Anal. HPLC indicated product to be >95% pure with R$_t$=48.08 min. ESI-MS m/z for C$_{57}$H$_{76}$N$_9$O$_{15}$S (MH$^+$), calcd 1158.5, found 1158.8.

N-Tritylglycine 4-Nitrophenylcarbonic Anhydride Solution

In a 10-mL round-bottomed flask equipped with a magnetic stir was dissolved 86.4 mg DMAP (N,N-dimethylaminopyridine) (0.708 mmol) in 1 mL EtOAc and 3 mL DCM. To this was added a solution of 36.2 mg 4-nitrophenylchloroformate (0.180 mmol) in 1 mL EtOAc, followed by a solution of 56.2 mg N-trityl glycine (Aldrich) (0.177 mmol) in 1 mL DCM. The reaction was then allowed to stir at RT for 15 min. The reaction was then concentrated in vacuo, then taken up in 1 mL DMF to afford the approximately 177 mM solution of N-tritylglycine 4-nitrophenylcarbonic anhydride containing approximately 531 mM DMAP.

Synthesis of Argatroban-AEA$_3$-βAla-Gly-OPh-CO-FIYEE-NH$_2$.2TFA

Figure 19:
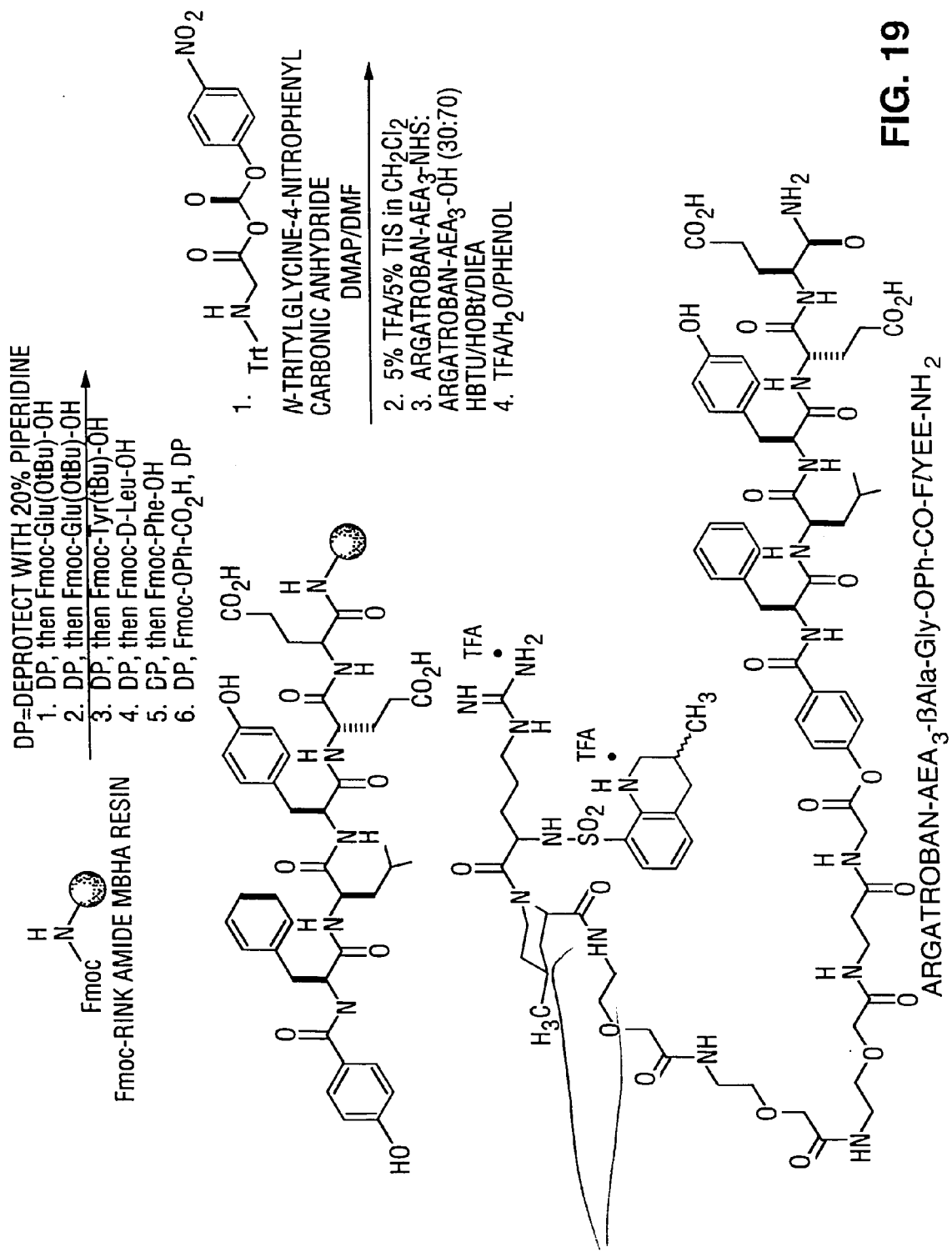
FIG. 19 is a reaction scheme setting forth the procedure for the synthesis of argatroban-AEA$_3$-βAla-Gly-OPh-CO-FIYEE-NH$_2$●2 TFA according to the invention.

The procedure followed for this synthesis is illustrated schematically in FIG. 19. A 0.035 mmol portion of the HO-Ph-CO-FIYEE-PS fragment was then transferred to a 4-mL solid phase reaction vessel and washed with three 1-mL portions of DMF. This was then shaken with approximately 1.0 mL of approximately 177 mM solution N-tritylglycine 4-nitrophenylcarbonic anhydride solution (0.177 mmol) with approximately 531 mM DMAP (0.531 mmol) for 2 h. This was then filtered and washed with six 2-mL portions of DMF and six 2-mL portions of DCM. The trityl group was then removed by vortexing a solution of 5% TFA/5% TIS in DCM (4×1 mL) for 1 min each. The resin was then washed with six 1-mL portions of DCM, six 1-mL portions of DMF, 1 mL of 2 M DIEA in NMP, and three 1-mL portions of DMF to afford a tan resin (the resulting resin showed a positive ninhydrin test). The resin was then treated with a solution of 38.0 mg of a 70:30 mixture of argatroban-AEA$_3$-βAla-OH: argatroban-AEA$_3$-βAla-NHS ester dissolved in a solution of 393 µL of 0.45 M HBTU/HOBt, 393 µL DMF, and 88.5 µL of 2 M DIEA in NMP for 1.25 h. The resin was washed with six 1-ml portions of DMF and six 1-mL portions of DCM to afford a tan resin (the resulting resin showed a negative ninhydrin test). The resin was then treated with two 1-mL portions of cleavage cocktail solution (10 mL TFA, 0.5 mL water and 0.5 mL TIS) for 1 h each. The combined cleavage filtrates were concentrated by rotary evaporation to 0.5 mL and crude product was then isolated by precipitation with 13 mL dry-ice cold $Et_2O$ followed by centrifugation. After decanting the supernatant, the resulting white solid was re-suspended in 13 mL dry-ice cold ether, centrifuged, and decanted two times. This was then dissolved in 2 mL of 0.045% TFA in $CH_3CN$ and 3 mL of 0.045% TFA in water, allowed to stand at RT for 1 h, frozen then lyophilized to afford 29.7 mg of a white solid. This was then dissolved in 4 mL of 0.045% TFA in $CH_3CN$ and 4 mL of 0.045% TFA in water and purified by preparative reverse-phase HPLC to afford 6.7 mg of argatroban-$AEA_3$-βAla-Gly-OPh-CO-FIYEE-$NH_2$.2 TFA as a white solid (0.003 mmol, 10%). Anal. HPLC indicated product to be >80% pure with $R_t$=54.77 min. ESI-MS m/z for $C_{81}H_{113}N_{17}O_{24}S$ (MH$^+$), calcd 1739.8, found MH$^{2+}$871.1.

Synthesis of Fluorescein-thiourea-$AEA_3$-Gly-OPh-CO-FIYEE-$NH_2$

Figure 20:
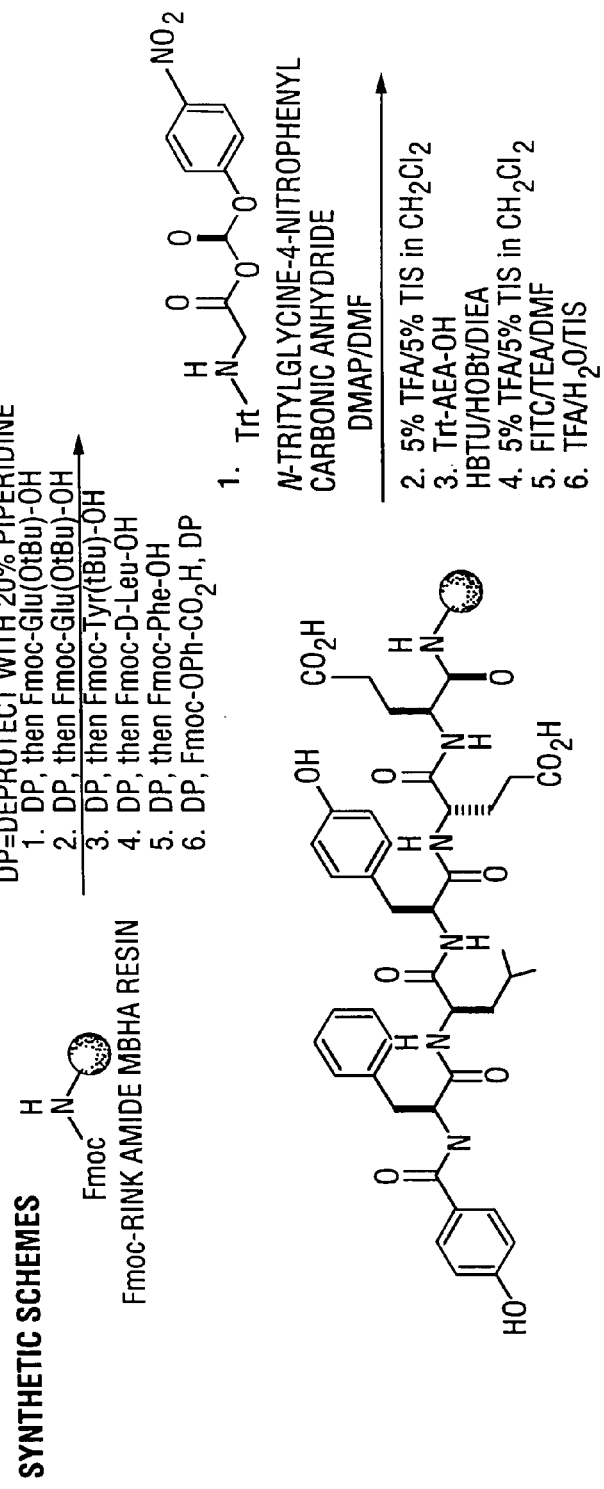
FIG. 20 is a reaction scheme setting forth the procedure for the synthesis of Fluorescein-thiourea-AEA-Gly-OPh-CO-FIYEE-NH$_2$ according to the invention.
Figure 20:
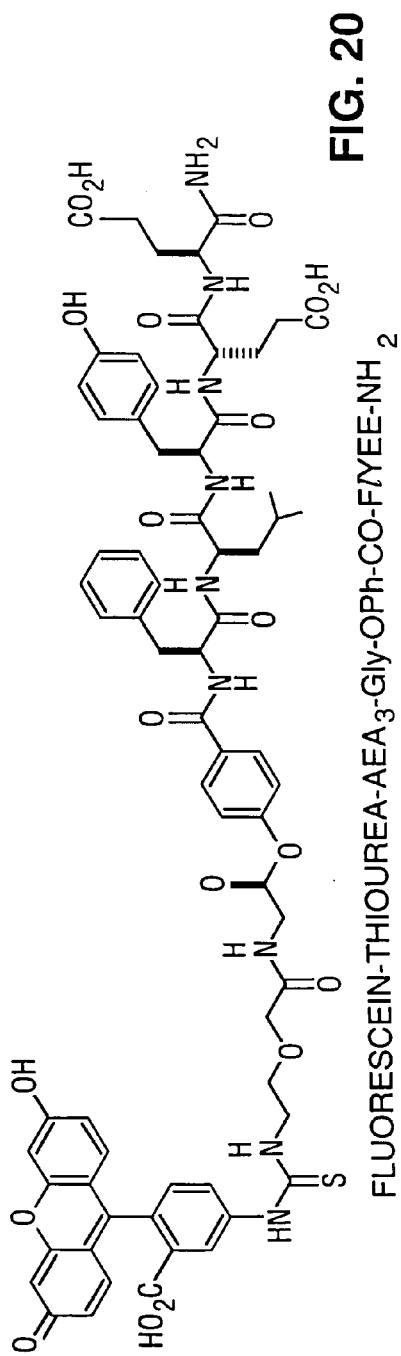

The procedure followed for this synthesis is illustrated schematically in FIG. 20. A 0.035 mmol portion of the HO-Ph-CO-FIYEE-PS fragment was then transferred to a 4-mL solid phase reaction vessel and washed with three 1-mL portions of DMF. This was then shaken with approximately 1.0 mL of approximately 177 mM solution N-tritylglycine 4-nitrophenylcarbonic anhydride solution (0.177 mmol) with approximately 531 mM DMAP (0.531 mmol) for 2 h. This was then filtered and washed with six 2-mL portions of DMF and six 2-mL portions of DCM. The trityl group was then removed by vortexing a solution of 5% TFA/5% TIS in DCM (4×1 mL) for 1 min each. The resin was then washed with six 1-mL portions of DCM, six 1-mL portions of DMF, 1 mL of 2 M DIEA in NMP, and three 1-mL portions of DMF to afford a tan resin (the resulting resin showed a positive ninhydrin test). The resin was then shaken with a solution of 64.0 mg N-trityl aminoethoxyacetic acid (Trt-AEA-OH) (0.177 mmol) dissolved in a solution of 393 μL of a 0.45 M HBTU/HOBt, 393 μL of DMF, and 88.5 μL of 2 M DIEA in NMP for 1 h. The resin was washed with six 1-ml portions of DMF and six 1-mL portions of DCM to afford a tan resin (the resulting resin showed a negative ninhydrin test). The trityl group was then removed by vortexing a solution of 5% TFA/5% triisopropylsilane (TIS) in DCM (4×1 mL) for 1 min each, then washed with six 1-mL portions of DCM, six 1-mL portions of DMF, 1 mL of 2 M DIEA in NMP, and three 1-mL portions of DMF to afford a tan resin (the resulting resin showed a positive ninhydrin test). The tan resin was then shaken with a solution of 50.3 mg fluorescein isothiocyanate isomer I (FITC) (0.116 mmol) and 11 μL TEA (0.079 mmol) for 10 min. The resin was filtered and washed with six 1-mL portions of DMF and six 1-mL portions of DCM to afford a tan resin (the resulting resin showed a negative ninhydrin test). The resin was then treated with two 1-mL portions of cleavage cocktail solution (10 mL TFA, 0.5 mL water and 0.5 mL TIS) for 1 h each. The combined cleavage filtrates were concentrated by rotary evaporation to 0.5 mL and crude product was then isolated by precipitation with 13 mL dry-ice cold $Et_2O$ followed by centrifugation. After decanting the supernatant, the resulting white solid was re-suspended in 13 mL dry-ice cold ether, centrifuged, and decanted two times. This was then dissolved in 2 mL of 0.045% TFA in $CH_3CN$ and 3 mL of 0.045% TFA in water and purified by preparative reverse-phase HPLC to afford 6.4 mg fluorescein-thiourea-$AEA_3$-Gly-OPh-CO-FIYEE-$NH_2$ as a yellow-orange solid (0.005 mmol, 13%). Anal. HPLC indicated product to be >95% pure with $R_t$=58.14 min. ESI-MS m/z for $C_{68}H_{70}N_9O_{20}S$ (MH$^+$), calcd 1364.4, found 1366.3, MH$^{2+}$ 683.9.

Example 4a

HSA Screening of Library at Level of 81 Compounds Per Well with a 1 Minute Quenching Time The S-linked library described in Example 1 was constructed and screened against HSA using the general experimental procedures described in the "General Library Screening" Section above. Using a 1 minute quenching time, the screening procedures were first carried out at the level of 81 compounds per well with 81 distinct wells. At this level of screening, (see FIG. 4) each well contains a mixture of compounds of the formula Biotin-S-Ph-C(O)—$O_1$—$O_2$—$X_1$—$X_2$—B—$NH_2$, with $X_1$ and $X_2$ fixed for each well and each well containing a mixture of the 81 combinations of possible $O_1$ and $O_2$ amino acids. B is fixed as glutamic acid. The amino acid residue at position $O_2$ is an L-amino acid; the amino acid residues at all other positions are D-amino acids. Quenching time was fixed at 1 minute.

A rapid quench (1 minute) destroys the slow unreacted library members, thus limiting nonspecific bonding due to reaction of the library members with other nucleophiles that compete with the same reactive functional group. Fast quenching is advantageous since it facilitates identification of a lead affinity group in spite of the limited amount of biotin added. ELISA assays were used and the optical density results shown in Table II were recorded. Table II shows sort values calculated as (ΔO.D.−2×S.D./(background O.D.) and represented in FIG. 4.

TABLE II

| l-amino acid at position $O_1$ | d-amino acid at position $O_2$ | | | | | | | | |
|---|---|---|---|---|---|---|---|---|---|
| | Glu | Gln | Arg | Met | Ser | Tyr | Leu | Phe | Trp |
| Glu | 1.3 | 0.8 | 1.2 | 0.9 | 1.0 | 1.3 | 0.4 | 1.1 | 1.4 |
| Gln | 2.0 | 0.9 | 1.4 | 1.2 | 1.4 | 1.3 | 0.7 | 1.2 | 1.1 |
| Arg | 1.0 | 0.6 | 2.2 | 1.0 | 1.0 | 1.5 | 1.1 | 1.2 | 1.3 |
| Met | 1.0 | 1.4 | 1.3 | 1.3 | 1.2 | 1.3 | 1.0 | 1.3 | 1.2 |
| Ser | 0.8 | 1.0 | 1.0 | 0.8 | 1.2 | 1.3 | 1.3 | 1.5 | 0.6 |
| Tyr | 1.3 | 1.2 | 1.4 | 1.1 | 1.0 | 0.8 | 1.7 | 1.4 | 1.5 |
| Leu | 1.2 | 1.0 | 1.2 | 1.3 | 1.4 | 0.3 | 1.1 | 1.4 | 1.4 |
| Phe | 1.4 | 0.8 | 1.4 | 1.4 | 1.2 | 0.7 | 3.5 | 1.2 | 1.5 |
| Trp | 1.2 | 1.4 | 1.3 | 1.1 | 1.5 | 1.0 | 0.7 | 1.5 | 1.5 |

From these results, it appears that molecules of the formula Biotin-S-Ph-C(O)—F-l-$X_1$—$X_2$-E-$NH_2$ show the highest measured optical density. The optical density (OD) is approximately proportional to the amount of biotin added at a site on a given target. An elevated OD can thus be explained as an elevated amount of biotinylation for a given well. The driving force behind the increased rate of biotinylation is explained in terms of the enhanced specificity brought by some of the most efficient affinity groups. As a result, an elevated OD for a given well may be the result of an enhanced specificity of addition for some of the members in that well. Using a one minute quench screening, biotin-S-Ph-C(O)—F-l-$X_1$—$X_2$-E-$NH_2$ shows high specificity for HSA based on optical density reading.

Example 4b

Figure 5:
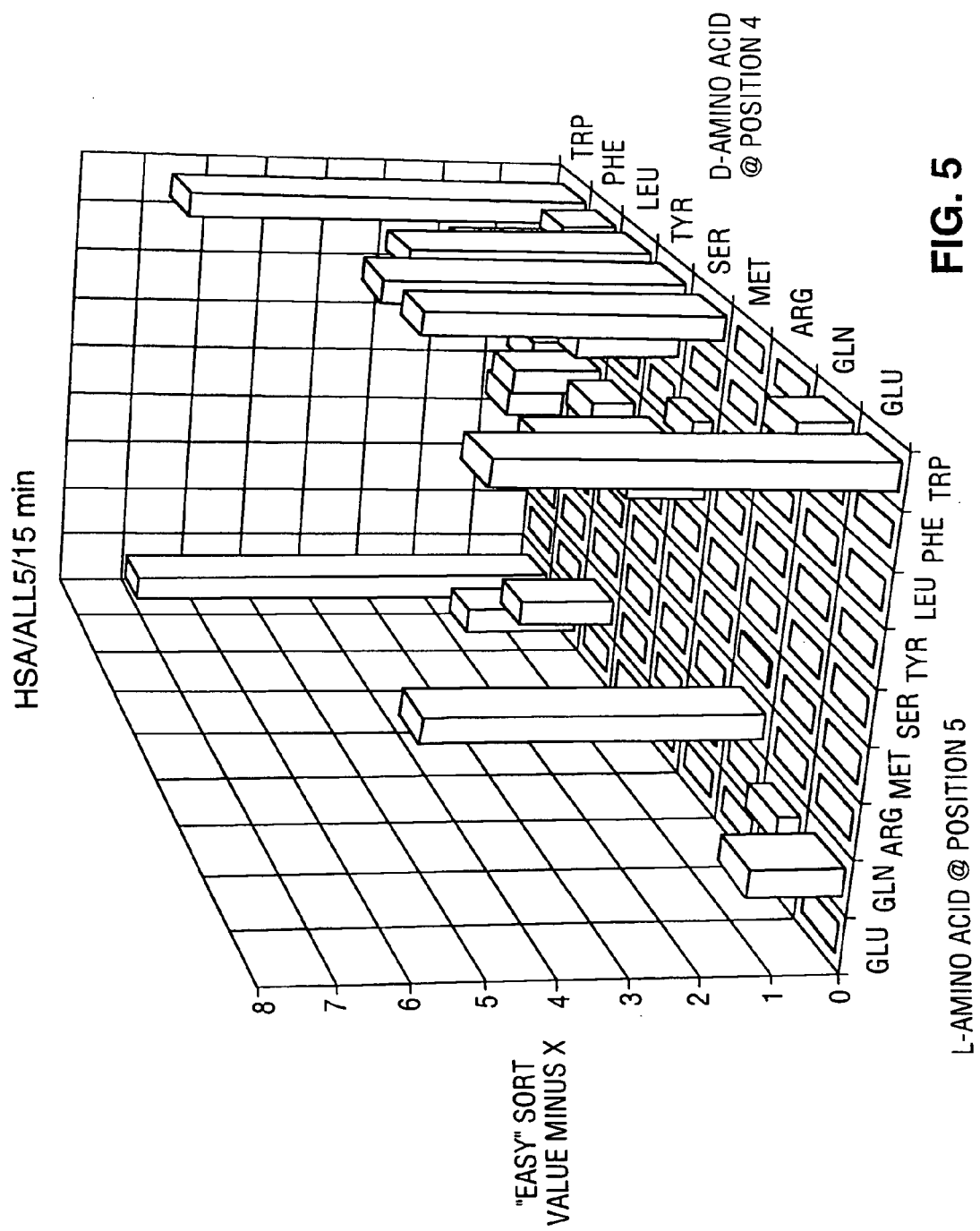
FIG. 5 shows optical density measurement for the screening of a library according to the present invention at the level of 81 compounds per well with a 15 minutes quenching.

HSA Screening of Library at Level of 81 Compounds Per Well with a 15 Minute Quenching Time The S-linked library described in Example 1 was constructed and screened against HSA using the general experimental procedures described in the "General Library Screening" section above. Using a 15 minute quenching time, the screening procedures were first carried out at the level of 81 compounds per well with 81 distinct wells. At this level of screening, (see FIG. 5) each well contains a mixture of compounds of the formula biotin-S-Ph-C(O)—$O_1$—$O_2$—$X_1$—$X_2$—B—$NH_2$, with $X_1$ and $X_2$ fixed for each well and each well containing a mixture of the 81 combinations of possible $O_1$ and $O_2$ amino acids. B is fixed as glutamic acid. The amino acid residue at position $O_2$ is an L-amino acid; the amino acid residues at all other positions are D-amino acids. Table III shows sort values calculated as ($\Delta$O.D.$-2\times$ S.D.)/(background O.D.). and represented in FIG. 5.

TABLE III

| l-amino acid at position | d-amino acid at position $O_2$ | | | | | | | | |
|---|---|---|---|---|---|---|---|---|---|
| $O_1$ | Glu | Gln | Arg | Met | Ser | Tyr | Leu | Phe | Trp |
| Glu | 3.3 | 3.6 | 3.6 | 1.2 | 2.3 | 3.6 | 3.2 | 6.1 | 11.3 |
| Gln | 5.6 | 4.6 | 3.0 | 2.1 | 2.1 | 3.7 | 5.8 | 4.2 | 4.0 |
| Arg | 3.5 | 3.2 | 9.4 | 2.3 | 3.0 | 3.9 | 3.9 | 3.3 | 3.4 |
| Met | 2.8 | 3.5 | 4.3 | 2.3 | 4.1 | 3.2 | 4.1 | 3.5 | 3.4 |
| Ser | 3.6 | 4.0 | 2.9 | 2.3 | 3.7 | 2.7 | 4.0 | 4.3 | 5.3 |
| Tyr | 3.9 | 3.5 | 2.8 | 2.6 | 5.4 | 6.3 | 4.9 | 5.8 | 4.9 |
| Leu | 3.9 | 3.1 | 3.2 | 2.6 | 4.5 | 3.3 | 2.4 | 4.2 | 4.6 |
| Phe | 4.0 | 3.7 | 3.1 | 2.8 | 4.3 | 6.0 | 4.4 | 4.1 | 6.1 |
| Trp | 9.8 | 5.1 | 3.1 | 3.2 | 8.8 | 9.0 | 8.2 | 5.1 | 10.9 |

Using a 15 minute quenching time, biotin-S-Ph-C(O)—W—W—$X_1$—$X_2$-E-$NH_2$ shows high specificity for HSA based on the readout of the optical density measured for each well.

Example 5

HSA Screening of Library at Level of 9 Compounds Per Well

Each particular set of candidate affinity groups, once identified, must be rescreened or deconvoluted. ELISA assays were carried out at the level of 9 compounds per well and 9 wells where the compounds have the formula biotin-S-Ph-C(O)-F-l-$X_1$—$X_2$-E-$NH_2$ with $X_1$ fixed for each well and each well containing the 9 possible $X_2$ amino acid residues. Construction of these compounds per well libraries is described below.

Figure 6A:
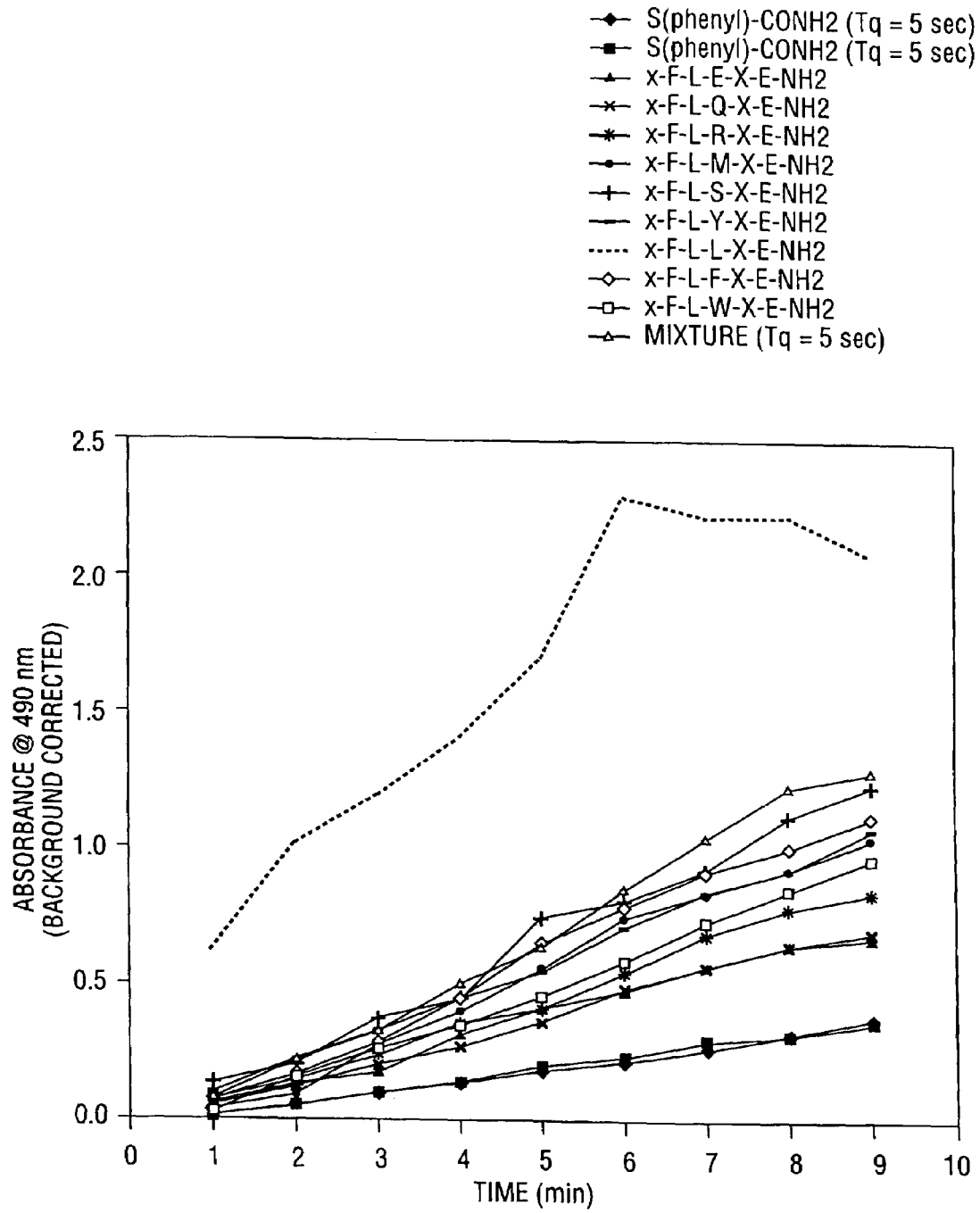
FIGS. 6a and 6b show optical density measurements for the screening of a library according to the present invention at the level of 9 compounds per well.
Figure 6B:
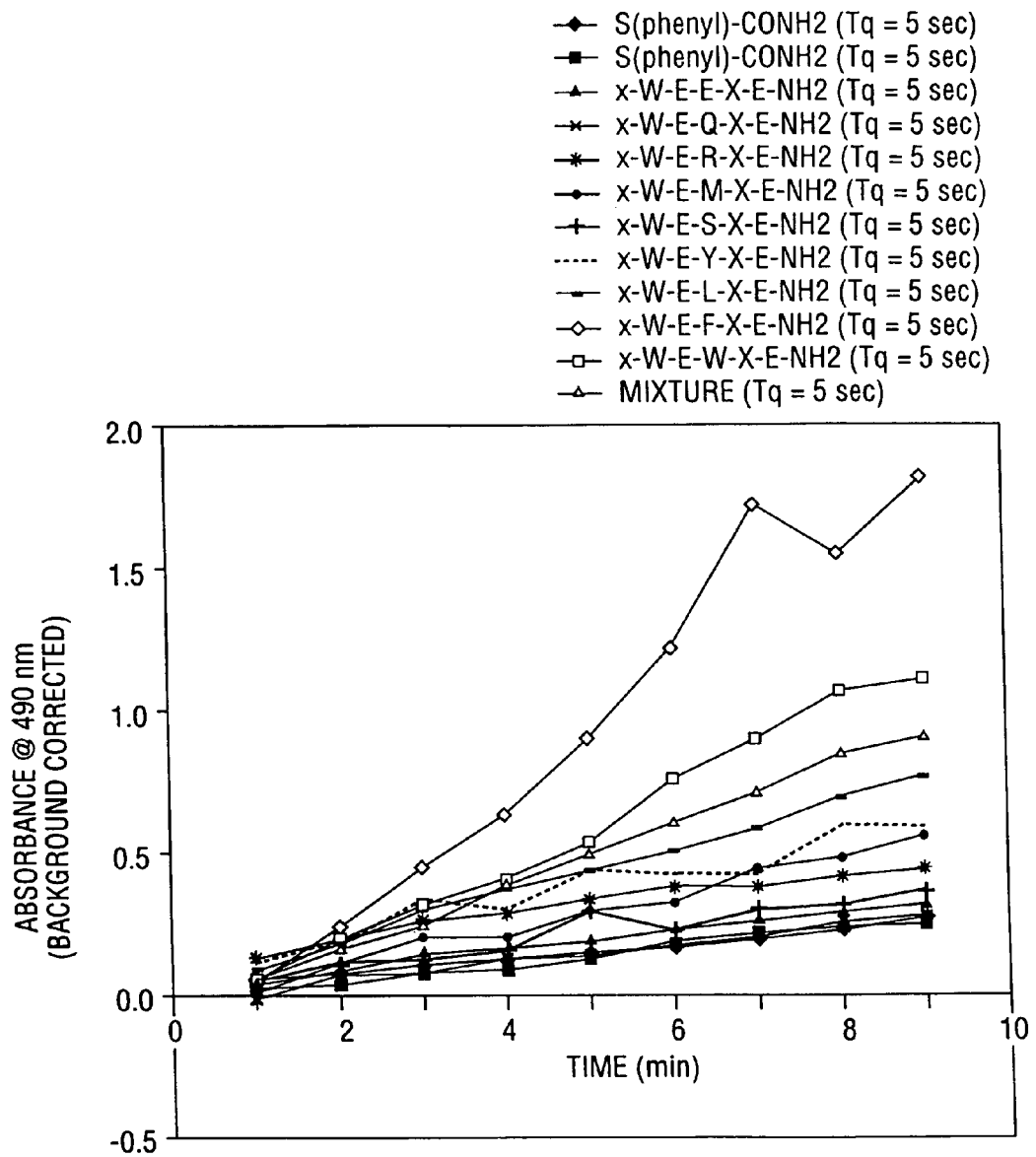

FIGS. 6a and 6b show optical density measurements from screening of the 9 wells. These results show that molecules of the formula Biotin-S-Ph-C(O)—F-l-Y-$X_2$-E-$NH_2$ show enhanced affinity for HSA. The binding determinant F-l-Y-$X_2$-E has SEQ ID NO:2.

Example 6

Biological Methods and Materials

Fraction V HSA (Calbiochem) was suspended in PBS (Sigma) at 15 or 600 μM and stored at −20° C. before use. Human plasma was obtained from Calbiochem, human serum from Sigma, and pig, dog, and human whole blood were obtained from healthy donors at Notre Dame Hospital in Montreal. The plasma was extracted by centrifugation of whole blood for 4 min at 500×g. D-biotin (Sigma) and NHS-LC-biotin (Pierce) were dissolved in DMSO (Sigma) at the required stock concentrations. Biotin-OPh-CO-FlYEE-$NH_2$, HO-Ph-CO-FlYEE-$NH_2$, biotin-OPh-CO—$NH_2$ were dissolved in DMSO at the required stock concentrations.

Biotinylation of Fraction V Human Serum Albumin, Human Serum and Whole Blood

In order to determine the specificity of FlYEE, either 100 or 600 μM of biotin-OPh-CO-FlYEE-$NH_2$ or biotin-OPh-CO—$NH_2$ was added to individual samples of whole blood, plasma or serum. The reaction samples were allowed to incubate for 1 h at RT or 37° C. For the whole blood sample, the plasma was extracted from whole blood at the end of reaction. Additional pig or dog plasma and fraction V HSA (600 μM final concentration) samples were prepared by mixing with 100 μm (final concentration) of biotin-OPh-CO-FlYEE-$NH_2$ or biotin-OPh-CO—$NH_2$ and allowed to incubate for 1 h at RT or 37° C. These additional samples were diluted 1/60 in PBS and analyzed directly on SDS-PAGE, immunoblot, ELISA, or frozen at −20° C. until use. As positive controls, 50 μM of NHS-LC-biotin (Pierce) and 100 μM of D-biotin were used. Protein assay was performed using BCA kit (Pierce).

Proteins were separated by SDS-PAGE under non-reducing conditions (Laemmli, 1970), transferred to 0.1 μM-pore nitrocellulose sheets (Schleicher and Schuell) and probed with peroxidase labeled streptavidin (Jackson Immuno Research). The biotinylated proteins were then revealed by an ECL detection kit (Pharmacia).

Competition ELISA Test

A solution of 100 μL rabbit polyclonal anti-human serum albumin. (Boehringer) diluted at 1/5000 in PBS was coated overnight at 4° C. onto ELISA plates (Nunc). These plates were then saturated with 5% BSA (Sigma) in PBS for 2 h at RT. For the competition test, varying concentrations of HO-Ph-CO-FlYEE-$NH_2$, 44 μM biotin-OPh-CO-FlYEE-$NH_2$, and 15 μM of fraction V HSA were incubated for 1 h at 37° C. To assess the ability of biotin-OPh-CO-FlYEE-$NH_2$ to displace HO-Ph-CO-FlYEE-$NH_2$, varying concentrations of HO-Ph-CO-FlYEE-$NH_2$ were incubated with HSA for 1 h at 37° C., then 44 μM of biotin-OPh-CO-FlYEE-$NH_2$ was added and allowed to incubate at 37° C. for 1 h. The reaction mixtures were then centrifuged through 30 kDa Centricon tubes (Sarthorious) to a volume of 50 μL, diluted with 500 μL of PBS, then re-concentrated to 50 μL. This process was then repeated and transferred to the ELISA plate previously coated with polyclonal anti-human serum albumin (procedure described above). These plates were then rinsed with PBS-Tween 20 (0.05%) three times, then with PBS. Peroxidase-labeled streptavidin (1:500, v/v, in PBS containing 0.05% BSA) was then added to the plates, allowed to incubate for 20 min at RT, rinsed with PBS-Tween 20 (0.05%) three times, and then with PBS. These rinsed plates were then treated with 100 μL of 0.5 mg/mL solution of o-phenylene diethylamine (Sigma) in a 50 mM (pH 5) $Na_2HPO_4$/citrate buffer for 6 min at RT, then 50 μL of 2N $H_2SO_4$ was added to quench the reaction. The plates were then read on a SpectraMax 250 at λ 490 nm.

Kinetic Study by ELISA Capture

A solution of 100 μL of human plasma was treated with 100 μM of NHS-LC-biotin, biotin-BMCC (Pierce), biotin- OPh-CO-FlYEE-NH$_2$ or biotin-OPh-CO—NH$_2$. The samples were then allowed to incubate at RT for 0, 5, 10, 15, 30 and 60 min, when 5 µL of each sample was diluted with 295 µL PBS and kept at −20° C. before use. The samples were then diluted to 2 µg/mL using PBS and transferred to an ELISA plate previously coated with polyclonal anti-human serum albumin (procedure described above). The plates were then rinsed with PBS-Tween 20 (0.05%) three times, and then with PBS. Goat polyclonal anti-biotin (Pierce) (1:200, v/v, in PBS containing 0.05% BSA) was then added to the plates, allowed to incubate for 1 h at RT, rinsed with PBS-Tween 20 (0.05%) three times, and then with PBS. The plates were then treated with 100 µL of peroxidase-conjugated rabbit anti-goat IgG (Jackson Immuno Research) diluted 1/100,000 with PBS for 20 min at RT. The plates were then rinsed with PBS-Tween 20 (0.05%) three times, and then with PBS. The plates were then treated with a 0.5 mg/mL solution of o-phenylene diethylamine (Sigma) in a 50 mM (pH 5) Na$_2$HPO$_4$/citrate buffer for 6 min at RT, then 50 µL of 2N H$_2$SO$_4$ was added to quench the reaction. The plates were then read on a SpectraMax 250 at λ 490 nm.

Example 7

Biological Results—Specificity of biotin-O-Ph-C(O)-FlYEE-NH$_2$ is Species Dependent Whole blood was incubated with biotin ester for 1 h at room temperature, then plasma was extracted by centrifugation. A 5 µg sample was separated by 8% SDS-PAGE and transferred onto blot. The immunoblot was blocked with 5% skim milk (Nestle) and then incubated with peroxidase labeled-streptavidin diluted at 1/5000 in PBS-BSA 0.5% for 20 min at RT. An ECL kit was used to detect peroxidase labeled-streptavidin on Hyperfilm ECL (Amersham), exposed for 1 min.

Example 8

Figure 7:
FIG. 7 shows an immunoblot in which human serum and plasma samples were labeled with two different concentrations of biotin-OPh-CO-NH$_2$ to assess compound lack of specificity in the absence of FIYEE peptide (having SEQ ID NO:1).

Biological Results—Non-Specificity of biotin-OPh-CO—NH$_2$: in Absence of "FIYEE" Peptide, (SEQ ID NO:1), the Biotinylated Compound Loses Specificity FIG. 7 shows an immunoblot in which human serum and plasma samples in lanes 1, 2 and 3 were labeled with 100 µM biotin-OPh-CO—NH$_2$ and samples in lanes 4, 5 and 6 with 600 µM biotin-OPh-CO—NH$_2$ for 1 h at 37° C. A 5 µg portion of each sample was separated by 8% SDS-PAGE and transferred onto blot. The immunoblot was blocked with 5% skim milk (Nestle) and then incubated with peroxidase labeled-streptavidin diluted at 1/5000 in PBS-BSA 0.5% for 20 min at RT. An ECL kit was used to detect peroxidase labeled-streptavidin on Hyperfilm ECL (Amersham), exposed for 1 min. Lanes 1 and 4 were fresh human plasma, lanes 2 and 5 were commercial human serum and lanes 3 and 6 were commercial human plasma.

Example 9

Figure 8:
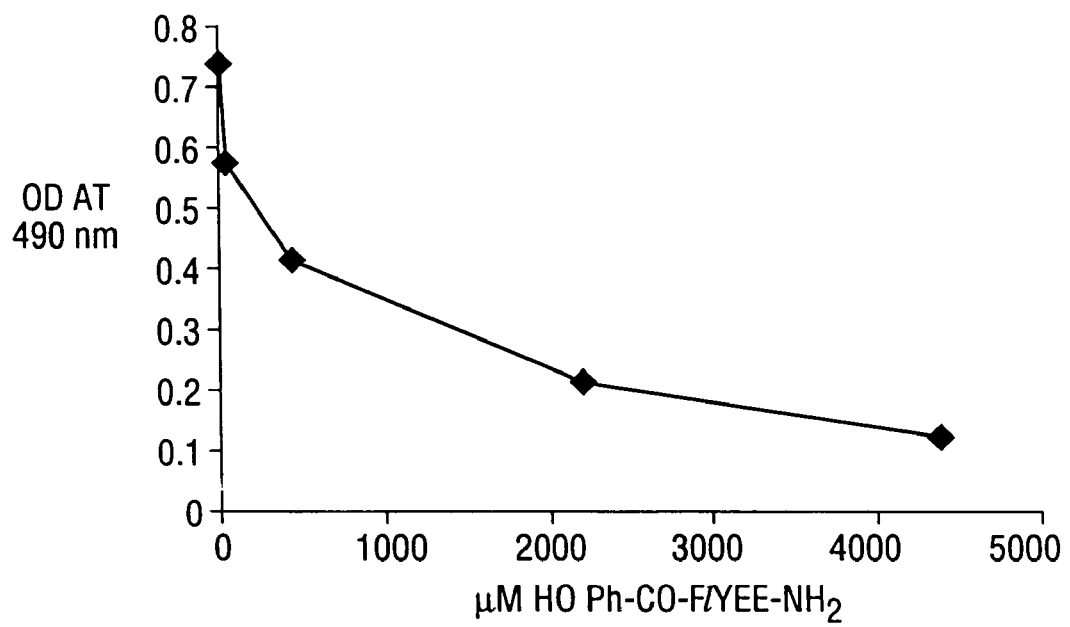
FIG. 8 shows a plot of optical density as a function of HO-Ph-CO-FIYEE-NH$_2$ concentration in an experiment to investigate competitive binding to HSA.

Biological Results—Competition of biotin-OPh-CO-FlYEE-NH$_2$ vs. HO-Ph-CO-FlYEE-NH$_2$ FIG. 8 plots optical density as a function of the concentration of HO-Ph-CO-FlYEE-NH$_2$. In these experiments, solutions of 0 to 100 molar excess HO-Ph-CO-FlYEE-NH$_2$ and 44 µM of biotin-OPh-CO-FlYEE-NH$_2$ were incubated with 15 µM of fraction V HSA for 1 h at 37° C. The HSA was captured on an ELISA plate initially coated with polyclonal anti-HSA, treated with peroxidase labeled streptavidin and OD read at 490 nm using SpectraMax 250.

Example 10

Figure 9:
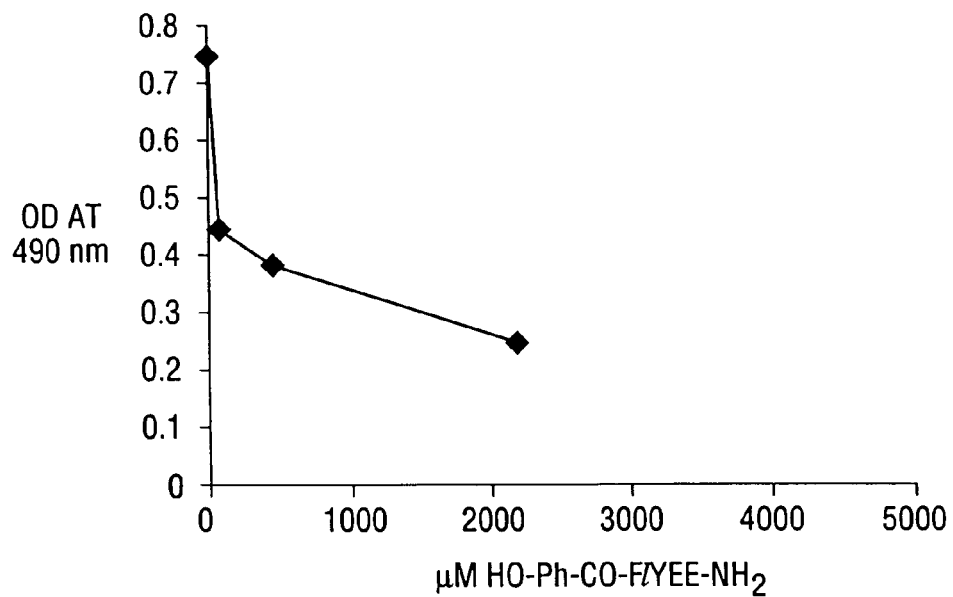
FIG. 9 shows a plot of optical density as a function of HO-Ph-CO-FIYEE-NH$_2$ concentration in an experiment to investigate competitive binding to HSA as compared to biotin-OPh-CO-FIYEE-NH$_2$.

Biological Results—Ability of biotin-OPh-CO-FlYEE-NH$_2$ to Displace HO-Ph-CO-FlYEE-NH$_2$ on HSA FIG. 9 shows a plot of optical density as a function of the concentration of HO-Ph-CO-FlYEE-NH$_2$. In these experiments, solutions of 0 to 50 molar excess HO-Ph-CO-FlYEE-NH$_2$ and 15 µM fraction V HSA were incubated for 1 h at RT when 44 µM of biotin-OPh-CO-FlYEE-NH$_2$, was added and reaction incubated for 1 h at 37° C. The HSA was captured on an ELISA plate initially coated with polyclonal anti-HSA, treated with peroxidase labeled streptavidin and OD read at 490 nm using SpectraMax 250.

Example 11

Biological Results—Rate of the Reactivity of biotin-OPh-CO-FlYEE-NH$_2$ in Plasma FIG. 9 shows the results of a kinetic study by ELISA capture experiment in which human plasma was treated with 100 µM biotin-OPh-CO-FlYEE-NH$_2$, biotin-OPh-CO—NH$_2$, NHS-LC-biotin or biotin-BMCC for 1 h at RT. At each time mentioned in the figure, 2 µg/mL of each sample was captured on an ELISA plate initially coated with polyclonal anti-HSA, treated with goat polyclonal anti-biotin, followed by peroxidase conjugated rabbit anti-goat IgG and OD read at 490 nm using SpectraMax 250.

Example 12

Biological Results—Kinetic Studies Using HPLC

Rate determination was performed on a Rainin Dynamax HPLC system equipped with a 4.6×250 mm Microsorb 300 Å C18 reverse phase column and UV detector at λ 214 and 245 nm running a gradient elution of 5–60% B (A: 0.045% TFA in H$_2$O and B: 0.045% TFA in CH$_3$CN) over 60 min at 0.5 mL/min. Each sample was prepared by mixing the appropriate amount of a stock solution of biotin-OPh-CO-FlYEE-NH$_2$ or biotin-OPh-CO—NH$_2$ in either 600 µM fraction V HSA or commercial human plasma and injecting 20 µL of this solution onto the column using an autosampler at various time intervals. The chromatograms were each integrated using identical data parameters and resulting calculated areas under each peak converted to concentrations and plotted against time.

Figure 11:
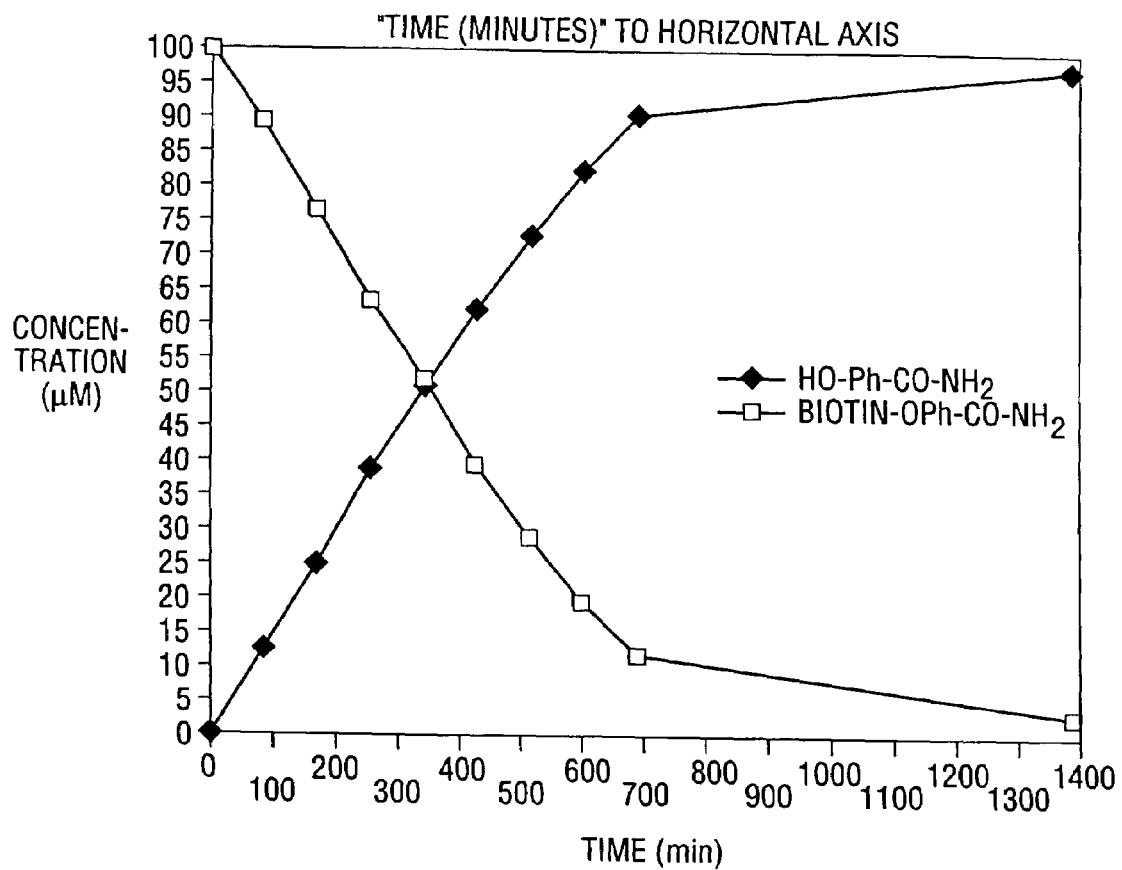
FIG. 11 shows a graph showing the rate of disappearance of biotin-OPh-CO—NH$_2$ and appearance of HO-Ph-CO—NH$_2$ as a result of reaction of HSA with biotin-OPh-CO—NH$_2$.

FIG. 11 plots the rate of disappearance of biotin-OPh-CO—NH$_2$ vs. time and the rate of appearance of the leaving group, HO-Ph-CO—NH$_2$, vs. time.

Figure 12:
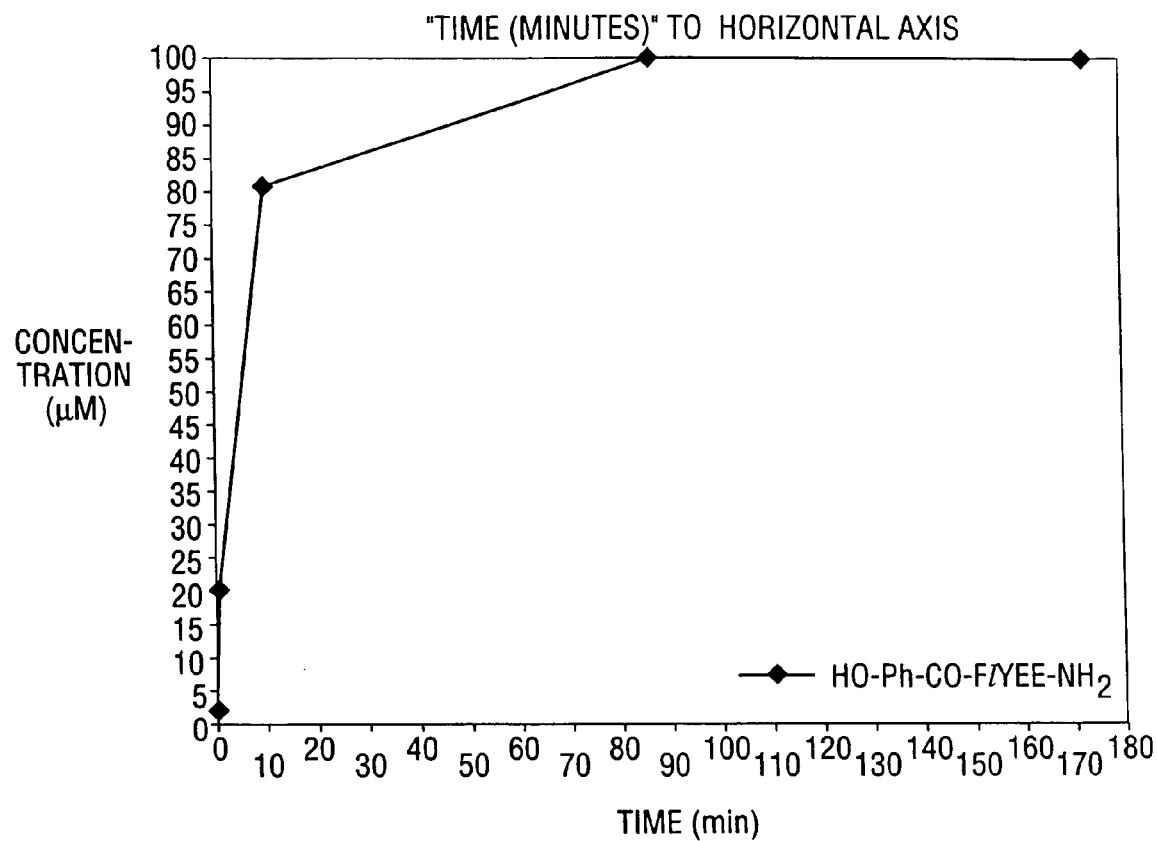
FIG. 12 shows a plot of the concentration of HO-Ph-CO-FIYEE-NH$_2$ resulting from the reaction of biotin-OPh-FIYEE-NH$_2$ in commercial human plasma as a function of time.

FIG. 12 plots the rate of appearance of the leaving group, HO-Ph-CO-FlYEE-NH$_2$, vs. time (seconds) as a result of the reaction of 100 µM biotin-OPh-CO-FlYEE-NH$_2$ in commercial human plasma. Due to overlapping peaks in the HPLC chromatogram, the rate of disappearance of biotin-OPh-CO-FlYEE-NH$_2$ cannot be determined.

Figure 13:
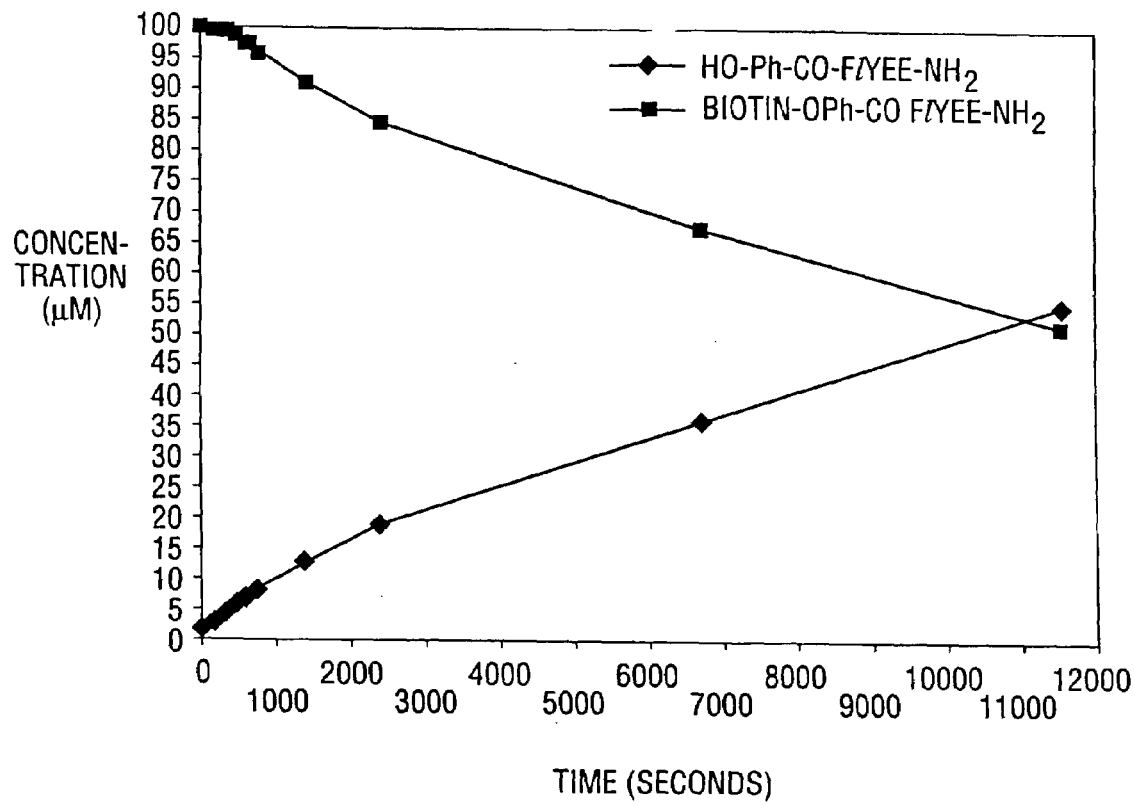
FIG. 13 shows a plot of the concentration of HO-Ph-CO-FIYEE-NH$_2$ and biotin-OPh-CO-FIYEE-NH$_2$ as a function of time during hydrolysis of biotin-OPh-CO-FIYEE-NH$_2$ in PBS (pH 7.4, RT).

FIG. 13 shows a plot of the rate of hydrolysis of biotin-OPh-CO-FlYEE-NH$_2$ vs. time (seconds) and the rate of appearance of the leaving group, HO-Ph-CO-FlYEE-NH$_2$, vs. time (seconds).

Figure 14:
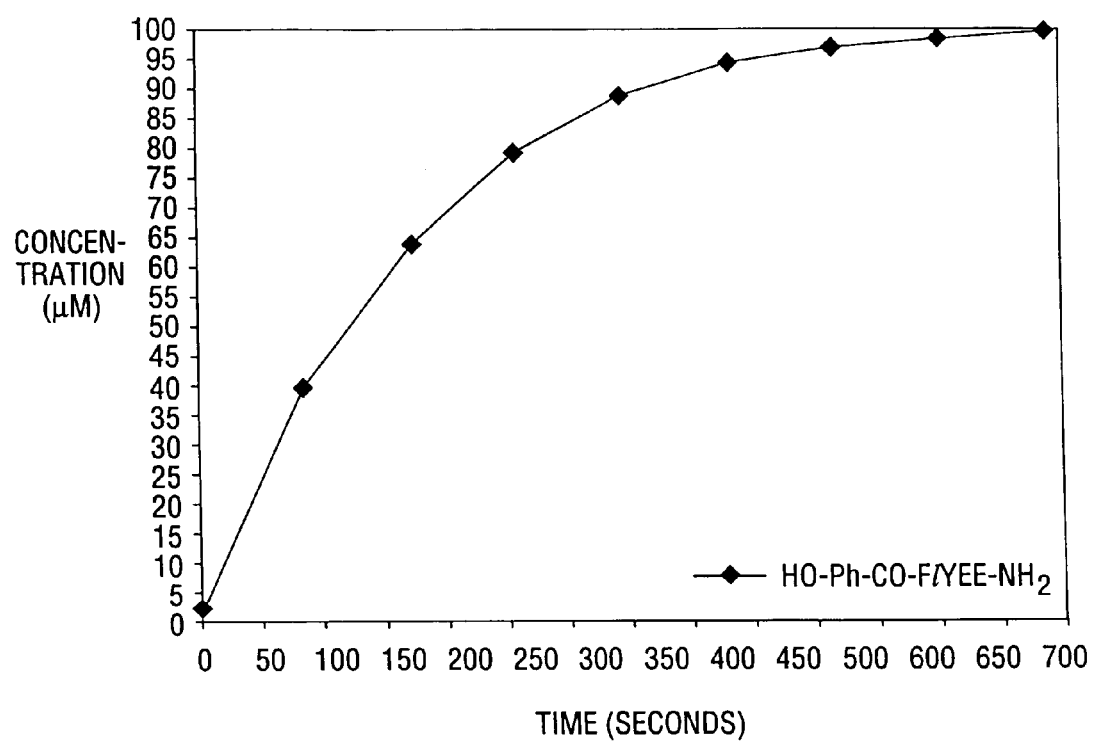
FIG. 14 shows a plot of the concentration of HO-Ph-CO-FIYEE-NH$_2$ as a function of time during reaction of biotin-OPh-CO-FIYEE-NH$_2$ with HSA in PBS (pH 7.4, RT).

FIG. 14 shows a plot of the rate of appearance of the leaving group, HO-Ph-CO-FlYEE-NH$_2$, vs. time (seconds). Due to overlapping peaks in the HPLC chromatogram, the rate of disappearance of biotin-OPh-CO-FlYEE-NH$_2$ cannot be determined.

FIG. 15 shows HPLC chromatographs of tryptic digest of HSA (top) and HSA:LC-biotin (bottom) where LC-biotin was introduced using LC-biotin-OPh-CO-FlYEE-NH$_2$. LC-biotin is biotin-NH—(CH$_2$)$_5$—C(O)—.

Discussion of Biological Results

Selectivity

Biotin-OPh-CO-FlYEE-NH$_2$ is selective to HSA. Immunoblots show the specificity of biotin-OPh-CO-FlYEE-NH$_2$ for human serum albumin (HSA) and not for pig or dog albumin in samples of whole blood.

Specificity

Figure 15A:
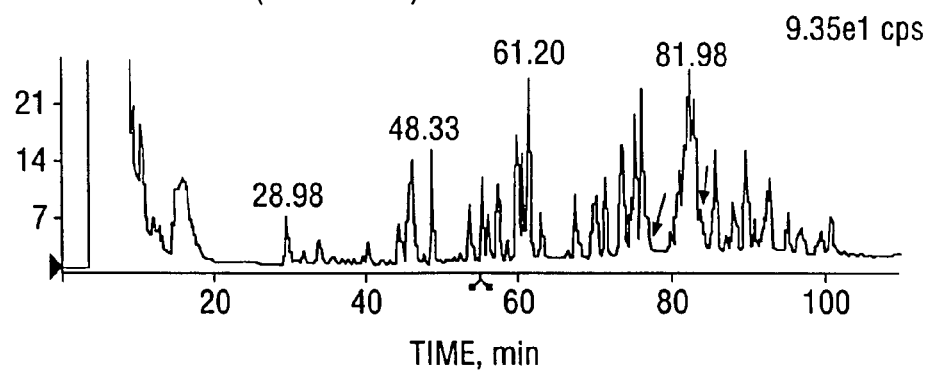
FIG. 15A shows an HPLC chromatograph of a tryptic digest of HSA.
Figure 15B:
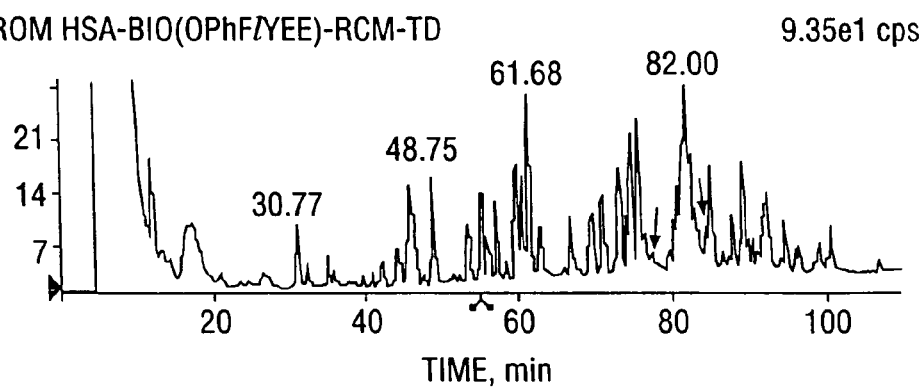
FIG. 15B shows an HPLC chromatograph of a tryptic digest of HSA:LC-biotin.

The specificity with which biotin-OPh-CO-FlYEE-NH$_2$ reacts with a specific lysine residue on HSA was determined by mass spectral analysis of a tryptic digest of LC-biotin conjugated to HSA by LC-biotin-OPh-CO-FlYEE-NH$_2$ (FIG. 15). Using LC -biotin-OPh-CO-FlYEE-NH$_2$ instead of biotin-OPh-CO-FlYEE-NH$_2$ facilitated a larger mass separation in the mass spectrum and identification of HSA from HSA:LC-biotin. The differences in the two chromatograms are not immediately obvious, however; careful analysis of these chromatograms reveals two new peaks (FIG. 15A and 15B, arrows indicate the new peaks at 78 and 85 minutes). Mass spectral analysis of the new peak at 78 min showed a new peptide fragment with a mass of 2887.6 which corresponds to a peptide sequence of $^{501}$EFNAETFNAET-FTFHADIBTLSELYSKER$^{521}$ (where B=carboxymethyl cysteine) SEQ ID NO:3) containing only one lysine residue where LC-biotin is attached, Lys$_{519}$. Mass spectral analysis of the new peak at 85 min showed a new peptide fragment with a mass of 5903.4, corresponding to a peptide sequence of: $^{476}$BBTESLVNRRPBFSALEVDETYVPK$^{500}$EFNAET FNAETFTFHADIBTLSEKER$^{521}$ (where B=carboxymethylcysteine) (SEQ ID NO:4) which contains two lysine residues (K$_{500}$ and K$_{519}$). This mass accounts only for the addition of one LC-biotin and since the fragment at 78 min contains only one Lys residue and LC-biotin is attached to it, and this peptide sequence contains the previous sequence, the only lysine residue in this sequence where biotin could be attached is Lys$_{519}$.

Because biotin-OPh-CO-FlYEE-NH$_2$ labels HSA selectively, is specific (FIG. 15) and biotin-OPh-CO—NH$_2$ does not label selectively (FIG. 7), it appears that biotin-OPh-CO—NH$_2$ will not label specifically and that the driving force to specificity is at least in part determined by the affinity portion of the molecule, the pentapeptide FlYEE-NH$_2$.

Reaction Kinetics

Prima facie evidence for the affinity of the FlYEE binding determinants for a specific site on the surface of HAS and its ability to direct pendant groups to such sites is supported by the results in FIGS. 8 and 9. The reaction of biotin-OPh-CO-FlYEE-NH$_2$ with HSA not only depends on concentration, but also on the amount of leaving group (HO-Ph-CO-FlYEE-NH$_2$) present. FIGS. 8 and 9 suggest competition for the active site on HSA between biotin-OPh-CO-FlYEE-NH$_2$ and the leaving group HO-Ph-CO-FlYEE-NH$_2$, which competition could effect the rate of binding and subsequent bonding of biotin to HSA. As shown in FIG. 8, direct competition of 0-100 molar excess of HO-Ph-CO-FlYEE-NH$_2$ and biotin-OPh-CO-FlYEE-NH$_2$ with 15 μM HSA indicates that the excess HO-Ph-CO-FlYEE-NH$_2$ occupies a specific binding site on HSA, thus preventing the binding and subsequent bonding of biotin-OPh-CO-FlYEE-NH$_2$. As FIG. 9 further illustrates, prior incubation of HO-Ph-CO-FlYEE-NH$_2$ with HSA prevents binding of biotin-OPh-CO-FlYEE-NH$_2$. This competition is observed only at the relatively higher concentrations of HO-Ph-CO-FlYEE-NH$_2$; between 1 to 5 molar excess of HO-Ph-CO-FlYEE-NH$_2$, competition has a very minor effect on the rate of reaction.

The influence of the affinity portion of the molecule (FlYEE-NH$_2$) on the rate of reaction is clearly seen by comparison of 100 μM biotin-OPh-CO—NH$_2$ and 600 μM HSA in PBS (FIG. 11) with 100 μM biotin-OPh-CO-FlYEE-NH$_2$ and 600 μM HSA in PBS (FIG. 14). The half-reaction for biotin-OPh-CO—NH$_2$ is about 330 min whereas that of biotin-OPh-CO-FlYEE-NH$_2$ is about 125 min. Under these reaction conditions, the rate of hydrolysis of the phenol ester is very slow (FIG. 13) and has a half-life of about 7.2 days. Not only does the affinity portion of the molecule greatly influence the rate of reaction; the reaction medium or the form of albumin has a tremendous effect on the rate of reaction. The half-reaction of with 100 μM biotin-OPh-CO-FlYEE-NH$_2$ in commercial human plasma is about 6 min. This dramatic change in rate is most likely due to conformational differences of HSA when in PBS and in plasma. This very rapid rate of reaction when in plasma is truly remarkable and is compelling evidence that an in vivo administration of a drug-OPh-CO-FlYEE-NH$_2$ molecule could be used as a possible therapeutic or diagnostic delivery agent.

Figure 10:
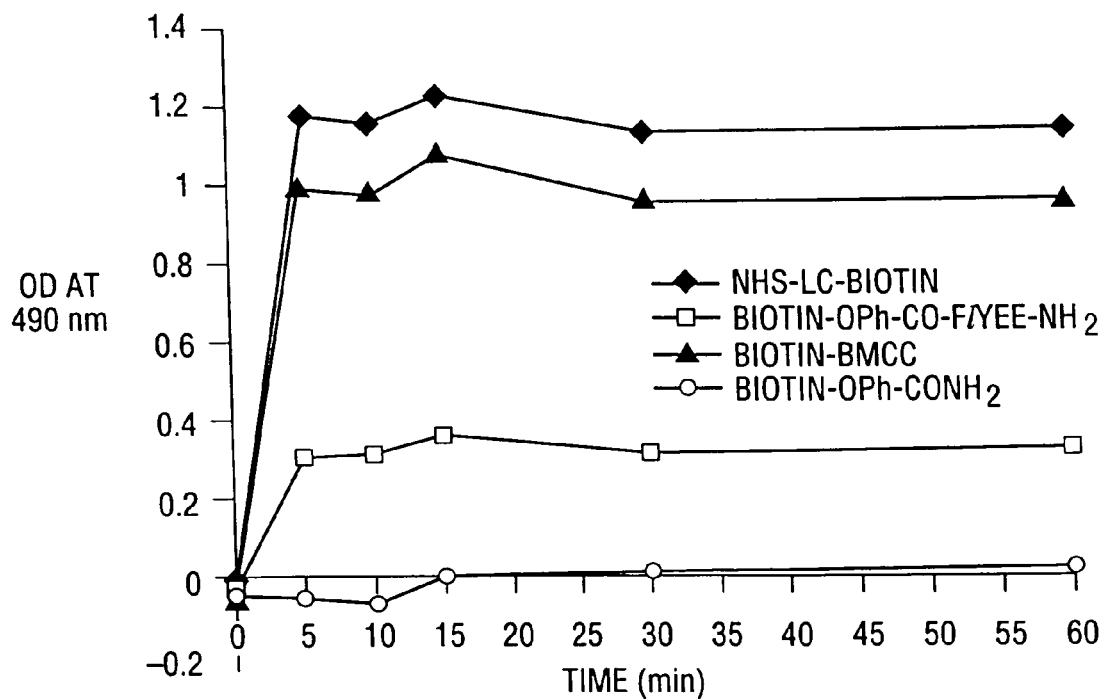
FIG. 10 shows a plot of optical density as a function of time for a kinetic study by ELISA capture in which human plasma was treated with biotin-OPh-CO-FIYEE-NH$_2$, biotin-OPh-CO—NH$_2$, NHS-LC-biotin or biotin-BMCC (BMCC is 1-biotinamido-4-[4'-(maleimidomethyl)cyclohexanecarboxamido]butane).

FIGS. 10 and 12 show the kinetic of addition of biotin-OPh-CO-FlYEE-NH$_2$ FIG. 10 shows the accelerated rate of biotin addition of biotin-OPh-CO-FlYEE-NH$_2$ when compared to biotin-OPh-CO—NH$_2$ (on the base line). As shown on FIG. 12, after only five minutes, more than half of a 100 μM biotin-OPh-CO-FlYEE-NH$_2$ has reacted with its protein target (in this case commercial human plasma).

We claim:

1. An affinity group comprising the sequence Phe-(D-Leu)-Tyr-Glu-Glu.

2. A compound comprising the affinity group of claim 1 wherein the compound has the formula E-$C_a$—R—$C_b$-A, wherein E is a therapeutic or diagnostic agent, R is a reactive group, $C_b$ and $C_a$ are optional first and second connecting groups, respectively, and A is the affinity group.

3. A compound according to claim 2, wherein the reactive group comprises a functional group selected from the group consisting of carboxy, phosphoryl, alkyl esters, thioesters, phosphoesters, ortho esters, imidates, mixed anhydrides, amides, thioamines and disulphides.

4. A compound according to claim 3, wherein $C_b$ is absent and the reactive group is bonded directly to the F residue in the affinity group.

5. A compound according to claim 4, wherein the reactive group is bonded to the F residue by an amide linkage.

6. A compound according to claim 2, wherein the reactive group has the formula —X—$R_1$—C(O)—, wherein $R_1$ comprises a substituted or unsubstituted aromatic group and X is selected from the group consisting of S, O and N.

7. A compound according to claim 6, wherein X is bonded directly to an aromatic carbon atom in $R_1$.

8. A compound according to claim 6, wherein $R_1$ is unsubstituted phenyl.

9. A compound according to claim 8, wherein —X— and —C(O)— are bonded to the phenyl in a para configuration.

10. A compound according to claim 6, wherein $R_1$ is phenyl substituted with one or more groups selected from the group consisting of a halogen, $NO_2$, $SO_2NH_2$, $SO_2NHF$, $CF_3$, $CCl_3$, $CBr_3$, C≡N, $SO_3H$, $CO_2H$, CHO, OH, $NHCOCH_3$, $OCH_3$, $CH_3$, and $CH_2CH_3$.

11. A compound according to claim 6, wherein said Phe of said affinity group comprises an amino group, and said reactive group comprises a carbonyl group, wherein a covalent bond is present between said amino group and said carbonyl group.

12. A compound according to claim 3, wherein $C_b$ is present.

13. A compound according to claim 10, wherein $C_b$ is bonded to the reactive group via an ester, thioester, amide, sulfonate ester or sulfonamide linkage.

14. A compound according to claim 12, wherein $C_b$ is bonded to the affinity group via an ester, thioester, amide, sulfonamide, urea, thiourea or carbamate linkage.

15. A compound according to claim 12, wherein $C_b$ comprises a backbone chain of between 1 and 25 atoms.

16. A compound according to claim 15, wherein $C_b$ comprises a backbone chain of between 2 and 16 carbon atoms.

17. A compound according to claim 12, wherein $C_b$ comprises an unsaturated carbon atom backbone chain of between 1 and 25 atoms.

18. A compound according to claim 2, wherein $C_a$ is present.

19. A compound according to claim 18, wherein $C_a$ is bonded to E by an ester, thioester, amide, sulfonate ester or sulfonamide linkage.

20. A compound according to claim 18, wherein $C_a$ is bonded to the reactive group by an ester, thioester, amide or sulfonate ester linkage.

21. A compound according to claim 18, wherein $C_a$ comprises a backbone chain of between 1 and 25 atoms.

22. A compound according to claim 21, wherein $C_a$ comprises a backbone chain of between 2 and 16 carbon atoms.

23. A compound according to claim 18, wherein $C_a$ comprises an unsaturated carbon atom backbone chain of between 1 and 25 atoms.

24. A compound according to claim 18, wherein the diagnostic agent comprises biotin.

25. A compound according to claim 24, wherein biotin is bonded directly to the reactive group by an ester, thioester or amide linkage.

26. A compound according to claim 24, wherein the reactive group has the formula —X-Ph-C(O)—, and wherein X is oxygen, sulfur or nitrogen.

27. A compound according to claim 26, wherein the —X— and —C(O)— on the phenyl group are bonded in a para configuration.

28. A compound according to claim 25, wherein $C_a$ is present.

29. A compound according to claim 28, wherein $C_a$ is bonded to the biotin group by an amide linkage.

30. A compound according to claim 28, wherein $C_a$ is —NH—$(CH_2)_n$—C(O)—, wherein n is an integer between 1 and 25.

31. A compound according to claim 30, wherein $C_a$ is —NH—$(CH_2)_5$—C(O)—.

32. A compound according to claim 30, wherein $C_a$ is —NH—$CH_2$—C(O)—.

33. The compound of claim 2, wherein said compound is selected from the group consisting of biotin-S-Ph-C(O)Phe-(D-Leu)-Tyr-Glu-Glu-$NH_2$, biotin-OPh-C(O)Phe-(D-Leu)-Tyr-Glu-Glu-$NH_2$, LC-biotin-S-Ph-C(O)Phe-(D-Leu)-Tyr-Glu-Glu-$NH_2$, biotin-Gly-OPh-C(O)Phe-(D-Leu)-Tyr-Glu-Glu-$NH_2$, fluorescein-Gly-OPh-Phe-(D-Leu)-Tyr-Glu-Glu-$NH_2$, LC-biotin-OPh-C(O)Phe-(D-Leu)-Tyr-Glu-Glu-$NH_2$, and fluorescein-thiourea-$AEA_3$-Gly-OPh-C(O)Phe-(D-Leu)-Tyr-Glu-Glu-$NH_2$.

* * * * *

SEQUENCE LISTING

<160> NUMBER OF SEQ ID NOS: 4

<210> SEQ ID NO 1
<211> LENGTH: 5
<212> TYPE: PRT
<213> ORGANISM: Artificial Sequence
<220> FEATURE:

-continued

```
<223> OTHER INFORMATION: Description of Artificial Sequence: synthetic
      peptide
<220> FEATURE:
<221> NAME/KEY: SITE
<222> LOCATION: 2
<223> OTHER INFORMATION: D configuration

<400> SEQUENCE: 1

Phe Leu Tyr Glu Glu
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: SITE
<222> LOCATION: 2
<223> OTHER INFORMATION: D configuration
<220> FEATURE:
<221> NAME/KEY: VARIANT
<222> LOCATION: 4
<223> OTHER INFORMATION: Xaa is Glu, Gln, Arg, Met, Ser, Tyr, Leu, Phe
      or Trp

<400> SEQUENCE: 2

Phe Leu Tyr Xaa Glu
1               5

<210> SEQ ID NO 3
<211> LENGTH: 29
<212> TYPE: PRT
<213> ORGANISM: Homo sapiens
<220> FEATURE:
<221> NAME/KEY: SITE
<222> LOCATION: 19
<223> OTHER INFORMATION: Cysteine is carboxymethyl cysteine

<400> SEQUENCE: 3

Glu Phe Asn Ala Glu Thr Phe Asn Ala Glu Thr Phe Thr Phe His Ala
1               5                   10                  15

Asp Ile Cys Thr Leu Ser Glu Leu Tyr Ser Lys Glu Arg
            20                  25

<210> SEQ ID NO 4
<211> LENGTH: 51
<212> TYPE: PRT
<213> ORGANISM: Homo sapiens
<220> FEATURE:
<221> NAME/KEY: SITE
<222> LOCATION: 1, 2, 12, 44
<223> OTHER INFORMATION: Cysteine is carboxymethyl cysteine

<400> SEQUENCE: 4

Cys Cys Thr Glu Ser Leu Val Asn Arg Arg Pro Cys Phe Ser Ala Leu
1               5                   10                  15

Glu Val Asp Glu Thr Tyr Val Pro Lys Glu Phe Asn Ala Glu Thr Phe
            20                  25                  30

Asn Ala Glu Thr Phe Thr Phe His Ala Asp Ile Cys Thr Leu Ser Glu
        35                  40                  45

Lys Glu Arg
   50
```